US011447814B2

(12) United States Patent
Chun et al.

(10) Patent No.: US 11,447,814 B2
(45) Date of Patent: *Sep. 20, 2022

(54) DETECTION OF TARGET NUCLEIC ACID SEQUENCE ON SOLID PHASE BY PTO CLEAVAGE AND EXTENSION USING HCTO ASSAY

(71) Applicant: SEEGENE, INC., Seoul (KR)

(72) Inventors: Jong Yoon Chun, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/028,817

(22) PCT Filed: Oct. 17, 2014

(86) PCT No.: PCT/KR2014/009774
§ 371 (c)(1),
(2) Date: Apr. 12, 2016

(87) PCT Pub. No.: WO2015/057008
PCT Pub. Date: Apr. 23, 2015

(65) Prior Publication Data
US 2016/0258007 A1 Sep. 8, 2016

(30) Foreign Application Priority Data
Oct. 18, 2013 (KR) .................. 10-2013-0124589

(51) Int. Cl.
| C12Q 1/70 | (2006.01) |
| C12N 9/00 | (2006.01) |
| C07H 21/04 | (2006.01) |
| C12Q 1/6832 | (2018.01) |
| C12Q 1/682 | (2018.01) |
| C12Q 1/6834 | (2018.01) |
| C12Q 1/6823 | (2018.01) |
| C12Q 1/6818 | (2018.01) |
| C12Q 1/6837 | (2018.01) |

(52) U.S. Cl.
CPC ........... *C12Q 1/6832* (2013.01); *C12Q 1/682* (2013.01); *C12Q 1/6818* (2013.01); *C12Q 1/6823* (2013.01); *C12Q 1/6834* (2013.01); *C12Q 1/6837* (2013.01)

(58) Field of Classification Search
None
See application file for complete search history.

(56) References Cited

U.S. PATENT DOCUMENTS

| 5,147,778 A | * | 9/1992 | Nietupski | ............ | C12Q 1/6813 |
| | | | | | 435/6.11 |
| 5,691,142 A | | 11/1997 | Dahlberg et al. | | |
| 6,444,661 B1 | * | 9/2002 | Barton | .................. | C07F 15/008 |
| | | | | | 514/185 |
| 8,809,239 B2 | * | 8/2014 | Chun et al. | .......... | C12Q 1/6837 |
| | | | | | 506/23 |
| 9,340,834 B2 | * | 5/2016 | Barany | ............... | C12Q 1/6827 |
| 2004/0023271 A1 | | 2/2004 | Kurn et al. | | |
| 2006/0040282 A1 | | 2/2006 | Monforte et al. | | |
| 2008/0193940 A1 | * | 8/2008 | Aivazachvili | ........ | C12Q 1/6823 |
| | | | | | 435/6.18 |
| 2017/0190745 A1 | * | 7/2017 | Kondo | ................. | C07K 14/005 |

FOREIGN PATENT DOCUMENTS

| JP | 2005536998 A | 12/2005 | | |
| JP | 2008509664 A | 4/2008 | | |
| WO | 2009155271 A1 | 12/2009 | | |
| WO | 2011001496 A1 | 1/2011 | | |
| WO | 2011027966 A2 | 10/2011 | | |
| WO | 2012096523 A2 | 7/2012 | | |
| WO | WO-2012096523 A2 | * | 7/2012 | ........... C12Q 1/6851 |
| WO | 2012150835 A2 | 11/2012 | | |

OTHER PUBLICATIONS

Sommer and Tautz, "Minimal homology requirement for PCR primers," Nucleic Acids Research, vol. 17, No. 16, 1989, p. 6749.*
("Oligonucleotide definition," Merriam-Webster.com; accessed Aug. 23, 2017.*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"Archaea," Wikipedia.com (accessed May 11, 2016).*
"Algae," Wikipedia.com (accessed Mar. 4, 2016).*
"Protozoa," Wikipedia.com (accessed May 11, 2016).*
"List of sequenced bacterial genomes" (Wikipedia.com; accessed Jan. 24, 2014).*
"Psst, the human genome was never completely sequenced", Sharon Begley, Statnews.com; Jun. 2017, pp. 2-8. (Year: 2017).*
Zeraati et al., ("I-motif DNA structures are formed in the nuclei of human cells", Nature Chemistry, vol. 10, Jun. 2018, pp. 631-637. (Year: 2018).*
"Viruses", Wikipedia.com, accessed Nov. 24, 2012. (Year: 2012).*
"How many species of bacteria are there", wisegeek.com; accessed Jan. 21, 2014. (Year: 2014).*

(Continued)

*Primary Examiner* — Bradley L. Sisson
(74) *Attorney, Agent, or Firm* — Gianna Julian-Arnold; Saul Ewing Arnstein & Lehr LLP

(57) ABSTRACT

The present invention relates to the detection of a target nucleic acid sequence from a DNA or a mixture of nucleic acids by a PCE-hCTO (PTO Cleavage and Extension using hCTO) assay on a solid phase. According to the present invention, the extended duplex is formed in a liquid phase in a target-dependent manner and then its presence is detected on a solid phase. Since hCTO is not immobilized onto a solid phase, the extended duplex is more effectively formed in a liquid phase.

15 Claims, 8 Drawing Sheets

Specification includes a Sequence Listing.

(56) References Cited

OTHER PUBLICATIONS

"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
Teixeira et al., "Using hominin introgression to trace modern human dispersals", PNAS, vol. 116, No. 31, Jul. 30, 2019, 15327-15332. (Year: 2019).*
"List of sequenced bacterial genomes", Wikipedia.com; accessed Jan. 24, 2014. (Year: 2014).*
Forster et al., "A human gut bacterial genome and culture collection for improved metagenomic analyses", Nature Biotechnology, vol. 37, Feb. 2019, 186-192. (Year: 2019).*
Zhu et al., "A Novel Coronavirus from Patients with Pneumonia in China, 2019", The New England Journal of Medicine, 328, 8, Feb. 20, 2020, pp. 727-733. (Year: 2020).*
Kim et al., "The Architecture of SARS-CoV-2 Transcriptome", Cell, 181, May 14, 2020, 914-921. (Year: 2020).*
International Search Report and Written Opinion, dated Feb. 2, 2015, issued in PCT/KR2014/009774.
Olivier, M.; The Invader assay of SNP genotyping; Elsevier, Mutation Research, vol. 573, 2005, pp. 103-110.
Lyamichev, V. et al.; Polymorphism identification and quantitative detection of genomic DNA by invasive cleavage of oligonucleotide probes; 1999 Nature America Inc., Nature Biotechnology, vol. 17, Mar. 1999, pp. 292-296.
Allawi, H., et al.; Quantitation of microRNAs using a modified Invader assay; RNA Society, vol. 10, 2004, pp. 1153-1161.

* cited by examiner

Immobilized Oligonucleotide (IO) on solid support

Immobilization of IO through its 3'-end

Immobilization of IO through its 5'-end

Hybridization

Primer extension & Cleavage of PTO

Hybridization of PTO fragment to hCTO & Extension

Hybridization of Duplex hCTO to IO and Detection

Hybridization

Primer extension & Cleavage of PTO

Hybridization of PTO fragment to hCTO & Extension

Hybridization of Duplex hCTO to IO and Detection

FIG. 4A

Fluorescent image

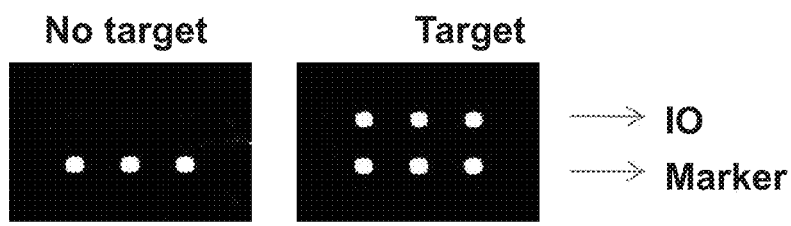

No target     Target     → IO
    → Marker

FIG. 4B

Fluorescence intensity

| Target [1] | Primers [2] | PTO [3] | hCTO [4] | RFU [5] |
|---|---|---|---|---|
| − | + | + | + | 836 (±175.1) |
| + | + | + | + | 65,261 (±1.5) |

[1] Target is genomic DNA of *Neisseria gonorrhoeae* gene.
[2] Primers are an upstream primer and a downstream primer for PCR.
[3] PTO (Probing and Tagging Oligonucleotide) has a fluorescent molecule at its 5'-end and is blocked with a carbon spacer at its 3'-end.
[4] hCTO (Hybridizing Capturing and Templating Oligonucleotide) having IO-hybridizing portion at its 5'-end portion has a blocker both at its 3'-end and in between IO-hybridization portion and templating portion.
[5] RFU represents relative fluorescence units.

DETECTION OF TARGET NUCLEIC ACID SEQUENCE ON SOLID PHASE BY PTO CLEAVAGE AND EXTENSION USING HCTO ASSAY

CROSS-REFERENCE TO RELATED APPLICATIONS

This application claims the priority of PCT/KR2014/009774, filed on Oct. 17, 2014, which claims priority to Korean Patent Application No. 10-2013-0124589, filed Oct. 18, 2013, the entire contents of each of which are hereby incorporated in total by reference.

SEQUENCE LISTING

This application incorporates by reference the Sequence Listing contained in an ASCII text file named "361406_00030_SeqList.txt" submitted via EFS-Web. The text file was created on Apr. 12, 2016, and is 3 kb in size.

BACKGROUND OF THE INVENTION

Field of the Invention

The present invention relates to detection of a target nucleic acid sequence by a PCE-hCTO (PTO Cleavage and Extension using hCTO) assay on a solid phase.

Description of the Related Art

DNA hybridization is a fundamental process in molecular biology and is affected by ionic strength, base composition, length of fragment to which the nucleic acid has been reduced, the degree of mismatching, and the presence of denaturing agents. DNA hybridization-based technologies would be a very useful tool in specific nucleic acid sequence determination and clearly be valuable in clinical diagnosis, genetic research, and forensic laboratory analysis.

However, the conventional methods and processes depending mostly on hybridization are very likely to produce false positive results due to non-specific hybridization between probes and non-target sequences. Therefore, there remain problems to be solved for improving their reliability.

Besides probe hybridization processes, several approaches using additional enzymatic reactions, for example, TaqMan™ probe method, have been suggested.

In TaqMan™ probe method, the labeled probe hybridized with a target nucleic acid sequence is cleaved by a 5' nuclease activity of an upstream primer-dependent DNA polymerase, generating a signal indicating the presence of a target sequence (U.S. Pat. Nos. 5,210,015, 5,538,848 and 6,326,145). The TaqMan™ probe method suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid sequence in close proximity such that binding of the nucleic acid polymerase to the 3'-end of the upstream primer puts it in contact with the 5'-end of the labeled probe to release the label. In addition, the TaqMan™ probe method discloses that the labeled probe at its 5'-end having a 5'-tail region not-hybridizable with a target sequence is also cleaved to form a fragment comprising the 5'-tail region.

There have been reported some methods in which a probe having a 5'-tail region non-complementary to a target sequence is cleaved by 5' nuclease to release a fragment comprising the 5'-tail region.

For instance, U.S. Pat. No. 5,691,142 discloses a cleavage structure to be digested by 5' nuclease activity of DNA polymerase. The cleavage structure is exemplified in which an oligonucleotide comprising a 5' portion non-complementary to and a 3' portion complementary to a template is hybridized with the template and an upstream oligonucleotide is hybridized with the template in close proximity. The cleavage structure is cleaved by DNA polymerase having 5' nuclease activity or modified DNA polymerase with reduced synthetic activity to release the 5' portion non-complementary to the template. The released 5' portion is then hybridized with an oligonucleotide having a hairpin structure to form a cleavage structure, thereby inducing progressive cleavage reactions to detect a target sequence.

U.S. Pat. No. 7,381,532 discloses a process in which the cleavage structure having the upstream oligonucleotide with blocked 3'-end is cleaved by DNA polymerase having 5' nuclease activity or FEN nuclease to release non-complementary 5' flap region and the released 5' flap region is detected by size analysis or interactive dual label. U.S. Pat. No. 6,893,819 discloses that detectable released flaps are produced by a nucleic acid synthesis dependent, flap-mediated sequential amplification method. In this method, a released flap from a first cleavage structure cleaves, in a nucleic acid synthesis dependent manner, a second cleavage structure to release a flap from the second cleavage structure and the release flaps are detected.

By hybridization of fluorescence-labeled probes in a liquid phase, a plurality of target nucleic acid sequences may be simultaneously detected using even a single type of a fluorescent label by melting curve analysis. However, the conventional technologies for detection of target sequences by 5' nuclease-mediated cleavage of interactive-dual labeled probes require different types of fluorescent labels for different target sequences in multiplex target detection, which limits the number of target sequences to be detected due to limitation of the number of types of fluorescent labels.

U.S. Pat. Appln. Pub. 2008-0241838 discloses a target detection method using cleavage of a probe having a 5' portion non-complementary to a target nucleic acid sequence and hybridization of a capture probe. A label is positioned on the non-complementary 5' portion. The labeled probe hybridized with the target sequence is cleaved to release a fragment, after which the fragment is then hybridized with the capture probe to detect the presence of the target sequence. In this method, it is necessary that an uncleaved/intact probe is not hybridized with the capture probe. For that, the capture probe having a shorter length has to be immobilized onto a solid substrate. However, such a limitation results in lower efficiency of hybridization on a solid substrate and also in difficulties in optimization of reaction conditions.

Therefore, there remain long-felt needs in the art to develop novel approaches for detection of a target sequence, particularly multiple target sequences on a solid phase by not only hybridization but also enzymatic reactions such as 5' nucleolytic reaction with enhanced accuracy in more convenient, reliable and reproducible hybridization manner. In addition, there remain long-felt needs in the art to develop novel approaches for detection of a target sequence with no limitation in terms of the number of types of labels (particularly, fluorescent labels).

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences, in which target detection is accomplished by probe hybridization, enzymatic reactions including 5' nucleolytic reaction, extension to form an extended duplex, and detection of extended duplex on a solid phase. The present protocols ensure detection of multiple target sequences on a solid phase with more improved accuracy and convenience.

Accordingly, it is an object of this invention to provide a method for detecting a target nucleic acid sequence from a DNA or a mixture of nucleic acids by a PCE-hCTO (PTO Cleavage and Extension using hCTO) assay on a solid phase.

It is another object of this invention to provide a kit for detecting a target nucleic acid sequence from a DNA or a mixture of nucleic acids by a PCE-hCTO (PTO Cleavage and Extension using hCTO) assay on a solid phase.

Other objects and advantages of the present invention will become apparent from the detailed description to follow taken in conjugation with the appended claims and drawings.

BRIEF DESCRIPTION OF THE DRAWINGS

FIG. 1A) and hCTO (Hybridizing-Capturing and Templating Oligonucleotide: FIG. 1B) and IO (immobilized oligonucleotide: FIG. 1C) used in the PCE-hCTO assay. Particularly, the 3'-ends of the PTO, hCTO and IO are blocked to prohibit their extension.

FIG. 2B: Primer extension & Cleavage of PTO; FIG. 2C: Hybridization of PTO fragment to hCTO & Extension; FIG. 2D: Hybridization of Duplex hCTO to IO and Detection). The IO-hybridizing portion is located at a 5'-end portion of the hCTO. The IO immobilized through its 3'-end onto a solid substrate comprises a sequence complementary to the IO-hybridizing portion of the hCTO.

FIG. 3B: Primer extension & Cleavage of PTO; FIG. 3C: Hybridization of PTO fragment to hCTO & Extension; FIG. 3D: Hybridization of Duplex hCTO to IO and Detection). The IO-hybridizing portion is located at a 5'-end portion of the hCTO and the IO immobilized through its 3'-end onto a solid substrate comprises a sequence complementary to the IO-hybridizing portion.

FIGS. 4A-4B represent detection results of the PCE-hCTO assay by using the hCTO having in its 5'-end portion the IO-hybridizing portion for analyzing the presence of the genomic DNA of *Neisseria gonorrhoeae* (FIG. 4A: Fluorescent image; FIG. 4B: Fluorescence intensity).

DETAILED DESCRIPTION OF THIS INVENTION

Figure 1A:
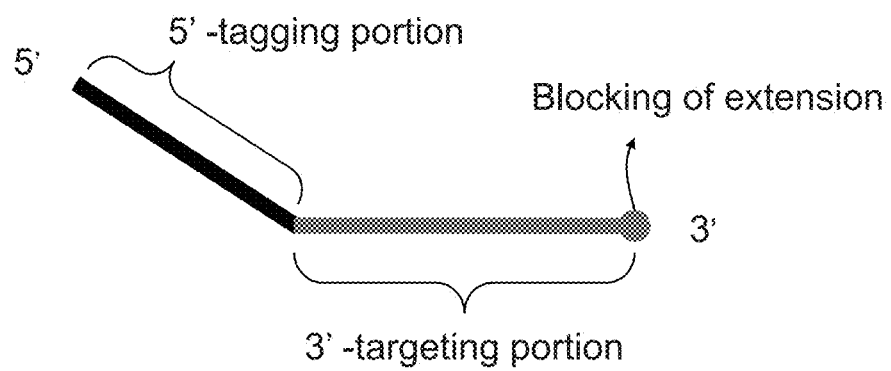
FIGS. 1A-1C show the schematic structures of PTO (Probing and Tagging Oligonucleotide.

The present invention provides novel methods and kits for detecting a target nucleic acid sequence by a PCE-hCTO (PTO Cleavage and Extension using hCTO) assay on a solid phase.

The present invention involves target-dependent enzymatic reactions as well as probe hybridization reaction.

I. Target Detection Using PCE-hCTO

In one aspect of the present invention, there is provided a method for detecting a target nucleic acid sequence from a DNA or a mixture of nucleic acids by a PCE-hCTO (PTO Cleavage and Extension using hCTO) assay on a solid phase, comprising:

(a) hybridizing the target nucleic acid sequence with an upstream oligonucleotide and a probing and targeting oligonucleotide (PTO); wherein the upstream oligonucleotide comprises a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO;

(c) hybridizing the fragment released from the PTO with a hybridizing-capturing and templating oligonucleotide (hCTO); wherein the hCTO comprises (i) a CTO in a 3' to 5' direction comprising a capturing portion comprising a nucleotide sequence complementary to the 5'-tagging portion or a part of the 5'-tagging portion of the PTO and a templating portion comprising a nucleotide sequence non-complementary to the 5'-tagging portion and the 3'-targeting portion of the PTO, and (ii) at the 3'- or 5'-end of the CTO an IO-hybridizing portion comprising a nucleotide sequence complementary to an immobilized oligonucleotide (IO) immobilized on a solid substrate; wherein the fragment released from the PTO is hybridized with the capturing portion of the hCTO;

(d) performing an extension reaction using the resultant of the step (c) and a template-dependent nucleic acid polymerase; wherein the fragment hybridized with the capturing portion of the hCTO is extended to form an extended duplex; wherein the extended duplex has a $T_m$ value adjustable by (i) a sequence and/or length of the fragment, (ii) a sequence and/or length of the hCTO or (iii) the sequence and/or length of the fragment and the sequence and/or length of the hCTO; wherein the IO-hybridizing portion of the hCTO remains in a single strand state;

(e) hybridizing the IO with the IO-hybridizing portion of the hCTO in the single strand state; wherein the IO immobilized on the solid substrate comprises a nucleotide sequence complementary to the IO-hybridizing portion of the hCTO; wherein the IO is hybridized with the IO-hybridizing portion of the hCTO to form an IO duplex; wherein the extended duplex provides a target signal by (i) at least one label linked to the fragment and/or the hCTO, (ii) a label incorporated into the extended duplex during the extension reaction, (iii) a label incorporated into the extended duplex during the extension reaction and a label linked to the fragment and/or the hCTO, or (iv) a label linked to the fragment or incorporated into the extended duplex during the extension reaction and a label linked to the IO; and (f) detecting the extended duplex on the solid phase by measuring the target signal at a pre-determined temperature at which both the extended duplex and the IO duplex is in a double strand state; wherein the presence of the extended duplex indicates the presence of the target nucleic acid sequence.

The present inventors have made intensive researches to develop novel approaches to detect target sequences with more improved accuracy and convenience, inter al/a, in a multiplex manner. As a result, we have established novel protocols for detection of target sequences, in which target detection is accomplished by probe hybridization, enzymatic reactions including 5' nucleolytic reaction, extension to form an extended duplex, and detection of extended duplex on a solid phase. The present protocols ensure detection of multiple target sequences on a solid phase with more improved accuracy and convenience.

The present inventors have already proposed a novel approach called PTOCE assay comprising successive events as follows in WO 2012/096523: cleavage of PTO (Probing and Tagging Oligonucleotide), extension on CTO (Capturing and Templating Oligonucleotide), target-dependent formation of extended duplex and detection of extended duplex. In the PTOCE assay, the CTO is immobilized onto a solid phase for target detection on a solid phase and the formation of the extended duplex is then detected.

The present inventors have made intensive studies to develop a novel target detection method on a solid phase in a multiplex manner with overcoming limitations to affect extension reaction, e.g., space limitation associated inherently with solid substrates which becomes troublesome in extension on the CTO immobilized onto a solid phase. Where one strand of the extended duplex in the PTOCE assay is hybridized with an oligonucleotide immobilized onto a solid phase, the hybridization is likely to be prevented by the presence of the other stand of the extended duplex. Furthermore, where the extended duplex is immobilized onto a solid phase, for example by using Biotin-Avidin/Streptavidin Systems, it is not possible to immobilize a certain extended duplex onto a desired location of the solid phase.

The present invention enables to overcome shortcomings described above by combining the following technical features: (i) target-dependent formation of the extended duplex, (ii) formation of the extended duplex in a liquid phase, (iii) use of hCTO enabling to have a single strand portion in the extended duplex, (iv) use of an immobilized oligonucleotide onto a solid phase comprising a nucleotide sequence complementary to the IO-hybridizing portion of the hCTO.

In considering the technical features, the present invention is named as a PCE-hCTO (PTO Cleavage and Extension using hCTO) assay.

While the present invention is based on our previous methods using the PTO and CTO, it ensures to more effectively detect target sequences on a solid phase with overcoming problems associated with solid phase application of our previous methods.

In the present invention, the extended duplex has an adjustable $T_m$ value which plays a crucial role in multiplex target detection and differentiation of target signals from non-target signals. Furthermore, because $T_m$ value of the hybrid between the IO and the IO-hybridizing portion of the hCTO is also adjustable, target sequences can be detected under various conditions sufficient to maintain the formation of the hybrid between the IO and the IO-hybridizing portion of the hCTO.

The present invention will be described in more detail as follows:

Step (a): Hybridization of an Upstream Oligonucleotide and a PTO with a Target Nucleic Acid Sequence According to the present invention, a target nucleic acid sequence is first hybridized with an upstream oligonucleotide and a PTO (Probing and Tagging Oligonucleotide).

The term used herein "target nucleic acid", "target nucleic acid sequence" or "target sequence" refers to a nucleic acid sequence of interest for detection, which is annealed to or hybridized with a probe or primer under hybridization, annealing or amplifying conditions.

The term used herein "probe" refers to a single-stranded nucleic acid molecule comprising a portion or portions that are substantially complementary to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

In a certain embodiment, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

The hybridization of a target nucleic acid sequence with the upstream oligonucleotide and the PTO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO) and the target nucleotide sequence. For instance, when a relatively short oligonucleotide is used, it is suitable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO comprise hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", for instance, perfectly complementary.

The 5'-tagging portion of the PTO comprises a nucleotide sequence non-complementary to the target nucleic acid sequence. The templating portion of the CTO (Capturing and Templating Oligonucleotide) has a nucleotide sequence non-complementary to the 5'-tagging portion and the 3'-targeting portion of the PTO. The term "non-complementary" is used herein to mean that primers or probes are sufficiently non-complementary not to hybridize selectively to a target nucleic acid sequence under the designated annealing conditions or stringent conditions, encompassing the terms "substantially non-complementary" and "perfectly non-complementary", for instance, perfectly non-complementary.

The term used herein "PTO (Probing and Tagging Oligonucleotide)" means an oligonucleotide comprising (i) a 3'-targeting portion serving as a probe and (ii) a 5'-tagging portion with a nucleotide sequence non-complementary to the target nucleic acid sequence, which is nucleolytically released from the PTO after hybridization with the target nucleic acid sequence. The 5'-tagging portion and the 3'-targeting portion in the PTO have to be positioned in a 5' to 3' order. The PTO is schematically illustrated in FIG. 1A.

In an embodiment, the hybridization in step (a) is performed under stringent conditions that the 3'-targeting portion is hybridized with the target nucleic acid sequence and the 5'-tagging portion is not hybridized with the target nucleic acid sequence.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides. The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length. The 5'-tagging portion may be in any lengths so long as it is specifically hybridized with the capturing portion of the CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. In certain embodiment, the 3'-end of the PTO is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO may be designed to have a hairpin structure.

The non-hybridization between the 5'-tagging portion of the PTO and the target nucleic acid sequence refers to non-formation of a stable double-strand between them under certain hybridization conditions. According to an embodiment of this invention, the 5'-tagging portion of the PTO not involved in the hybridization with the target nucleic acid sequence forms a single-strand. Where the 5'-tagging portion of the PTO per se can form a hairpin structure, it is not involved in the hybridization with the target nucleic acid sequence but forms a hairpin structure. In such case, the 5'-tagging portion is considered to form a single strand with reference to the target nucleic acid sequence.

The upstream oligonucleotide is located upstream of the PTO.

In addition, the upstream oligonucleotide or its extended strand hybridized with the target nucleic acid sequence induces cleavage of the PTO by an enzyme having a 5' nuclease activity.

The induction of the PTO cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO sufficient to induce the PTO cleavage by an enzyme having a 5' nuclease activity, the enzyme bound to the upstream oligonucleotide digests the PTO with no extension reaction. In contrast, where the upstream oligonucleotide is positioned distantly to the PTO, an enzyme having a polymerase activity (e.g., template-dependent polymerase) catalyzes extension of the upstream oligonucleotide (e.g., upstream primer) and an enzyme having a 5' nuclease activity bound to the extended product digests the PTO.

Therefore, the upstream oligonucleotide may be located relatively to the PTO in two fashions. The upstream oligonucleotide may be located adjacently to the PTO sufficient to induce the PTO cleavage in an extension-independent manner. Alternatively, the upstream oligonucleotide may be located distantly to the PTO sufficient to induce the PTO cleavage in an extension-dependent manner.

The term used herein "adjacent" with referring to positions or locations means that the upstream oligonucleotide is located adjacently to the 3'-targeting portion of the PTO to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to an embodiment, the upstream oligonucleotide is located distantly to the PTO sufficient to induce the PTO cleavage in an extension-dependent manner.

According to an embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-end part of the 3'-targeting portion of the PTO. In certain embodiment, the overlapped sequence is 1-10 nucleotides, 1-5 nucleotides or 1-3 nucleotides in length. Where the upstream oligonucleotide has a partial-overlapped sequence with the 5'-end part of the 3'-targeting portion of the PTO, the 3'-targeting portion is partially digested along with the 5'-tagging portion in the cleavage reaction of the step (b). In addition, the overlapped sequence permits to cleave a desired site of the 3'-targeting portion.

According to an embodiment, the upstream primer induces through its extended strand the cleavage of the PTO by the enzyme having the 5' nuclease activity.

The conventional technologies for cleavage reactions by upstream oligonucleotides may be applied to the present invention, so long as the upstream oligonucleotide induces cleavage of the PTO hybridized with the target nucleic acid sequence to release a fragment comprising the 5'-tagging portion or a part of the 5'-tagging portion of the PTO. For example, U.S. Pat. Nos. 5,210,015, 5,487,972, 5,691,142, 5,994,069 and 7,381,532 and U.S. Appln. Pub. No. 2008-0241838 may be applied to the present invention.

According to an embodiment, the method is performed in the presence of a downstream primer. The downstream primer generates additionally a target nucleic acid sequence to be hybridized with the PTO, enhancing sensitivity in target detection. For example, where the upstream oligonucleotides is an upstream primer and an enzyme having a 5' nuclease activity is DNA polymerase, the downstream primer generates additionally a target nucleic acid sequence to be hybridized with the PTO by DNA polymerase and then the fragments are more released, thereby enhancing sensitivity in target detection.

According to an embodiment, when the upstream primer and the downstream primer are used, a template-dependent nucleic acid polymerase is additionally employed for extension of the primers.

According to an embodiment, the upstream oligonucleotide (upstream primer or upstream probe), the downstream primer and/or 5'-tagging portion of the PTO have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35:6e40(2007)).

According to an embodiment, the 3'-targeting portion of the PTO has a modified dual specificity oligonucleotide (mDSO) structure developed by the present inventor. The modified dual specificity oligonucleotide (mDSO) structure shows significantly improved target specificity compared with conventional probes (see WO 2011/028041).

Step (b): Release of a Fragment from the PTO Cleavage

Afterwards, the resultant of the step (a) is contacted to an enzyme having a 5' nuclease activity under conditions for cleavage of the PTO. The PTO hybridized with the target nucleic acid sequence is digested by the enzyme having the 5' nuclease activity to release a fragment comprising the 5'-tagging portion or a part of the 5'-tagging portion of the PTO.

The term used herein "conditions for cleavage of the PTO" means conditions sufficient to digest the PTO hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, $MgCl_2$ and temperature.

Figure 2A:
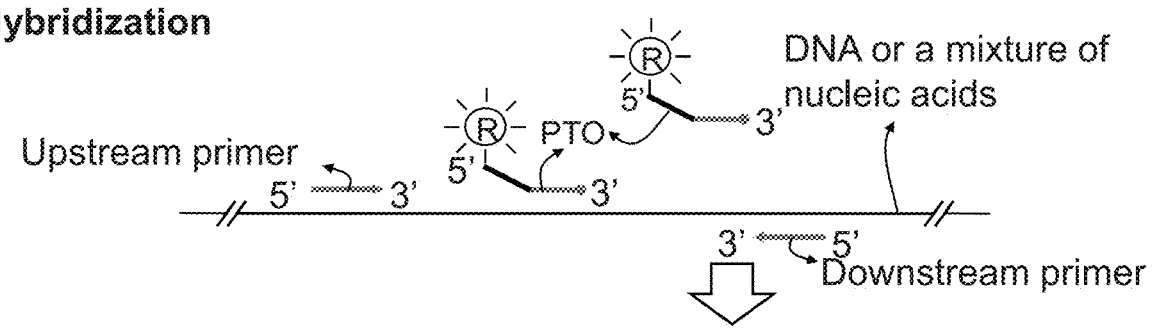
FIGS. 2A-2D represent schematically an embodiment of the PCE-hCTO assay using a single label linked to the 5'-end of the PTO (FIG. 2A: Hybridization.
Figure 2B:
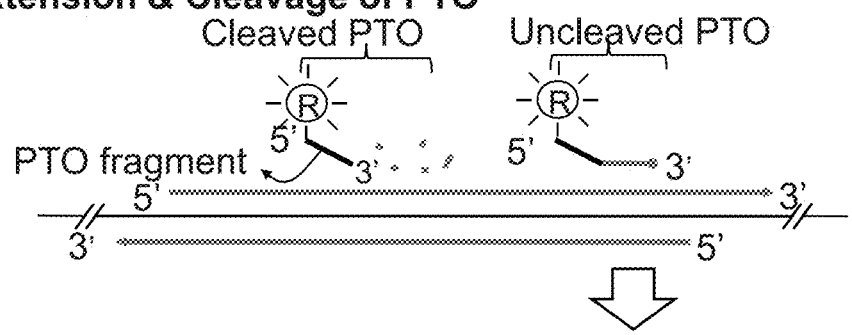
Figure 2C:
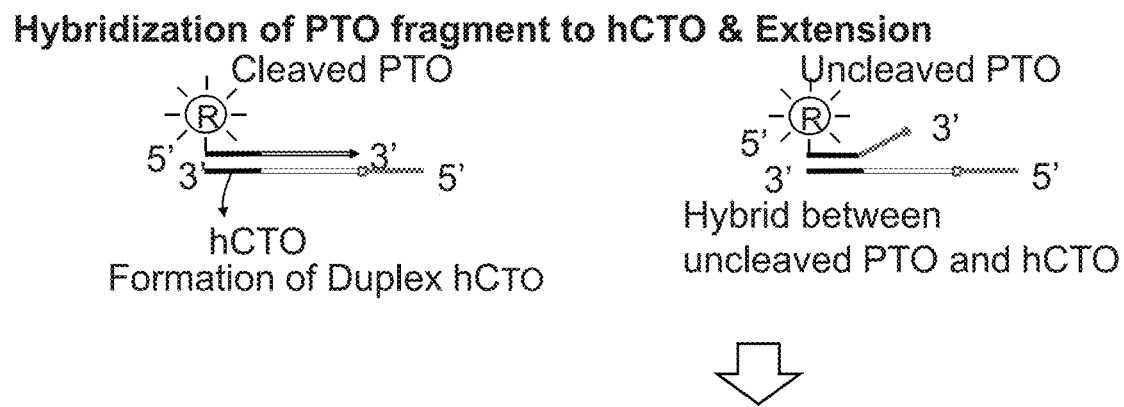
Figure 2D:
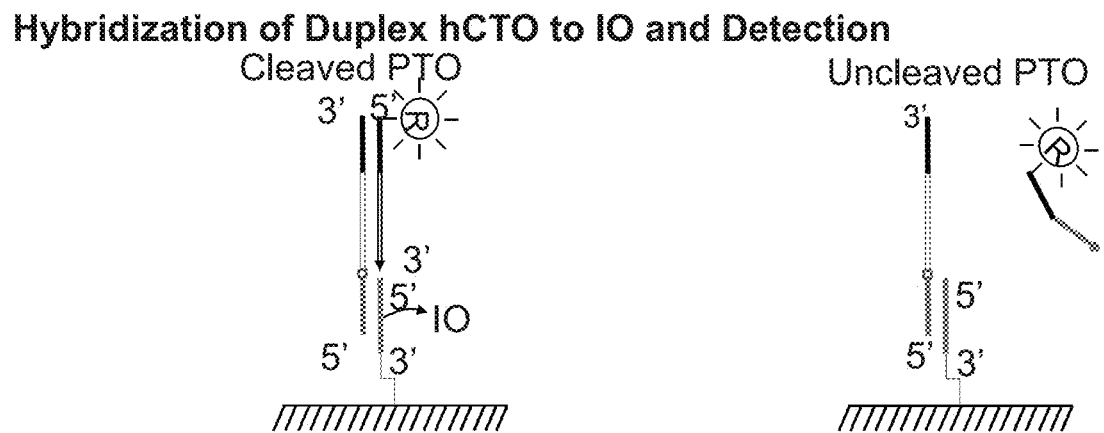
Figure 3A:
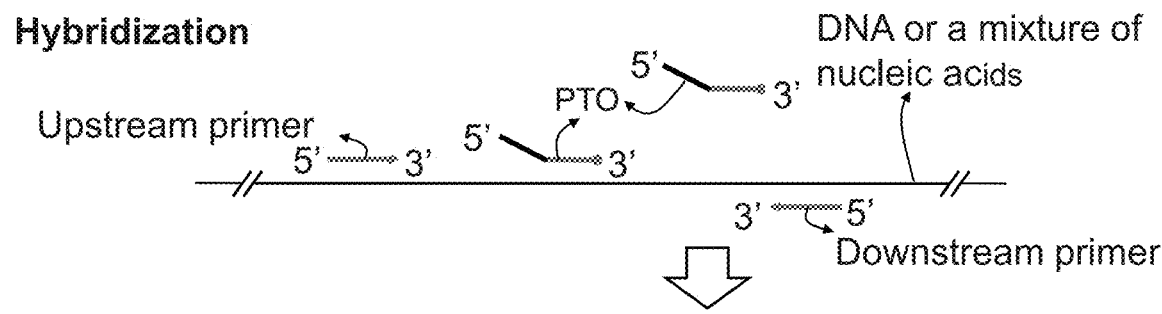
FIGS. 3A-3D represent schematically an embodiment of the PCE-hCTO assay by using a label incorporated into the extended duplex during the extension reaction in which the hCTO having iso-dC residue in its templating portion and the reporter-iso dGTP (FIG. 3A: Hybridization.
Figure 3B:
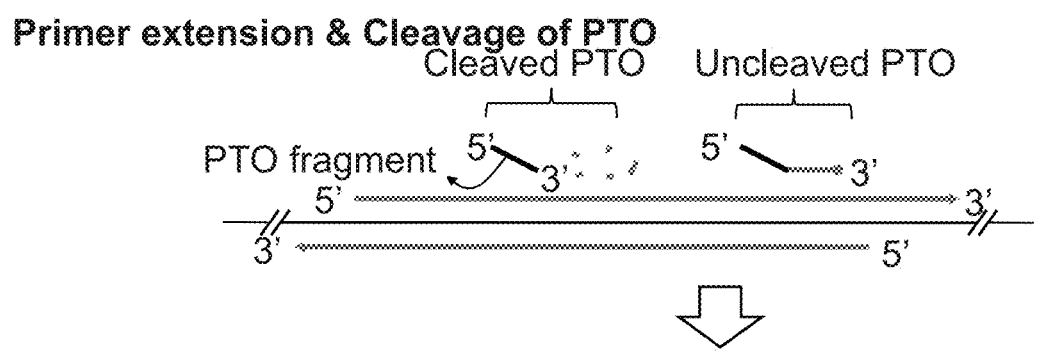
Figure 3C:
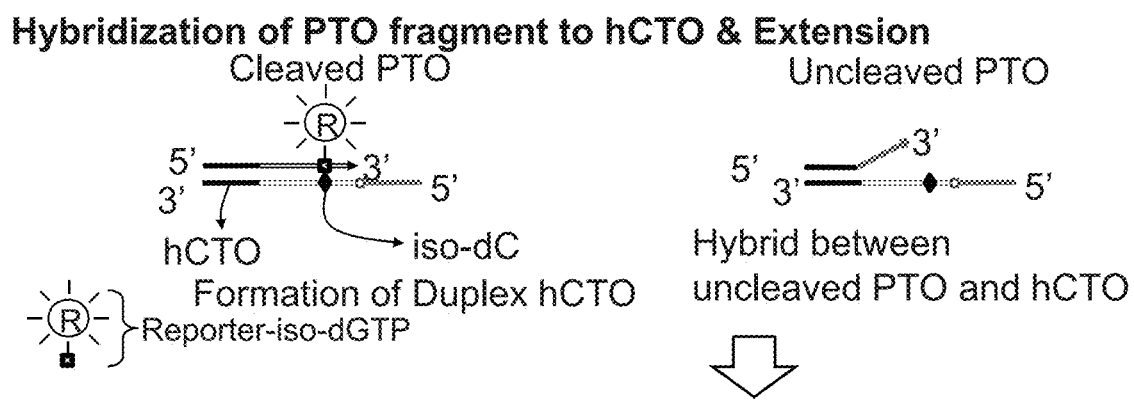
Figure 3D:
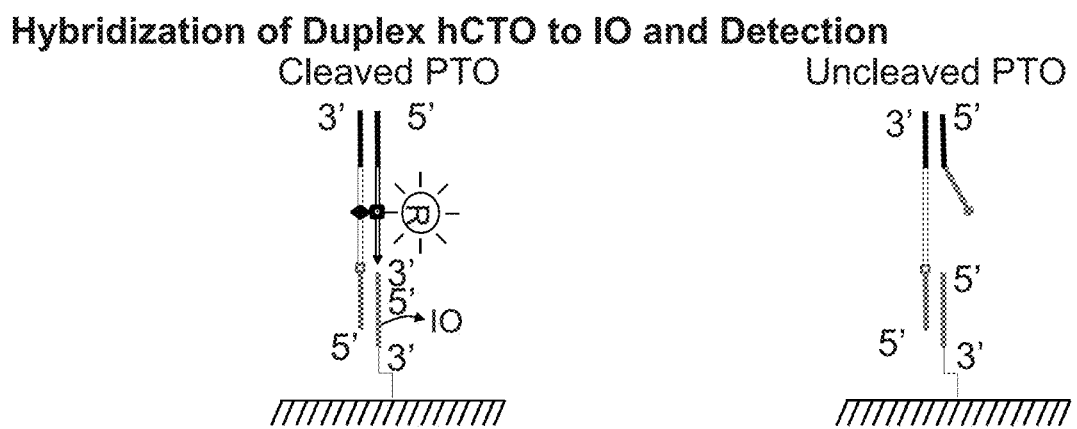

When the PTO is hybridized with the target nucleic acid sequence, its 3'-targeting portion is involved in the hybridization and the 5'-tagging portion forms a single-strand with no hybridization with the target nucleic acid sequence (see FIG. 2A). As such, an oligonucleotide comprising both single-stranded and double-stranded structures may be digested using an enzyme having a 5' nuclease activity by a variety of technologies known to one of skill in the art.

The cleavage sites of the PTO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO, releasing a fragment comprising the 5'-tagging portion or a part of the 5'-tagging portion.

Briefly, there may be three sites of cleavage in the step (b). Firstly, the cleavage site is a junction site between a hybridization portion of the PTO (3'-targeting portion) and a non-hybridization portion (5'-tagging portion). The second cleavage site is a site located several nucleotides in a 3'-direction apart from the 3'-end of the 5'-tagging portion of the PTO. The second cleavage site is located at the 5'-end part of the 3'-targeting portion of the PTO. The third cleavage site is a site located several nucleotides in a 5'-direction apart from the 3'-end of the 5'-tagging portion of the PTO.

According to an embodiment, the initial site for the cleavage of the PTO by the template-dependent polymerase having the 5' nuclease activity upon extension of the upstream primer is a starting point of the double strand between the PTO and the target nucleic acid sequence or a site 1-3 nucleotides apart from the starting point.

In this regard, the term used herein "a fragment comprising the 5'-tagging portion or a part of the 5'-tagging portion of the PTO" in conjunction with cleavage of the PTO by the enzyme having the 5' nuclease activity is used to encompass (i) the 5'-tagging portion, (ii) the 5'-tagging portion and the 5'-end part of the 3'-targeting portion and (iii) a part of the 5'-tagging portion. In this application, the term "a fragment comprising the 5'-tagging portion or a part of the 5'-tagging portion of the PTO" may be also described as "fragment" or "PTO fragment".

According to an embodiment, the PTO has a blocker portion containing as a blocker at least one nucleotide resistant to cleavage by the enzyme having 5' nuclease activity and the blocker portion is used to control an initial cleavage site and/or successive cleavages. For example, to induce cleavage at the junction site between a hybridization portion of the PTO (3'-targeting portion) and a non-hybridization portion (5'-tagging portion), the 5'-end part of 3'-targeting portion of PTO may be blocked with blockers. The number of blockers contained in the blocker portion may be not limited, including 1-10, 2-10, 3-8 or 3-6 blockers. The blockers present in the PTO may be in a continuous or intermittent manner, suitably a continuous manner. The nucleotides as blockers with a backbone resistant to the 5' to 3' nuclease activity include any one known to one of skill in the art. For example, it includes various phosphorothioate linkages, phosphonate linkages, phosphoroamidate linkages and 2'-carbohydrates modifications. According to an embodiment, nucleotides having a backbone resistant to the 5' to 3' nuclease activity include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-3-D-ribofuranosyl) modification.

According to an embodiment, a nucleotide as a blocker includes LNA (locked nucleic acid).

The term "part" used in conjunction with the PTO or CTO such as the part of the 5'-tagging portion of the PTO, the 5'-end part of the 3'-targeting portion of the PTO and the 5'-end part of the capturing portion of the CTO refers to a nucleotide sequence composed of 1-40, 1-30, 1-20, 1-15, 1-10 or 1-5 nucleotides, suitably 1, 2, 3 or 4 nucleotides.

According to an embodiment, the enzyme having the 5' nuclease activity is DNA polymerase having a 5' nuclease activity or FEN nuclease, suitably a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis, Thermis flavus, Thermococcus literalis, Thermus antranikianli, Thermus caldophilus, Thermus chliarophilus, Thermus flavus, Thermus igniterrae, Thermus lacteus, Thermus oshimai, Thermus ruber; Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus baross, Thermococcus gorgonarius, Thermotoga maritima, Thermotoga neapolitana, Thermosipho africanus, Pyrococcus woese, Pyrococcus horikoshil, Pyrococcus abyssi, Pyrodictium occultum, Aquifex pyrophilus* and *Aquifex aeollieus*. In certain embodiment, the thermostable DNA polymerase is Taq polymerase.

Alternatively, the present invention may employ DNA polymerases having a 5' nuclease activity modified to have less polymerase activities.

According to an embodiment, FEN (flap endonuclease) nuclease used is a 5' flap-specific nuclease.

The FEN nuclease suitable in the present invention comprises FEN nucleases obtained from a variety of bacterial species, including *Sulfolobus solfataricus, Pyrobaculum aerophilum, Thermococcus iltoralis, Archaeaglobus veneficus, Archaeaglobus profundus, Acidianus brierlyl, Acidianus ambivalens, Desulfurococcus amylolyticus, Desulfurococcus mobilis, Pyrodictium brocki, Thermococcus gorgonarius, Thermococcus zilligii, Methanopyrus kandler, Methanococcus igneus, Pyrococcus horikoshii, Aeropyrum pernix,* and *Archaeaglobus veneficus*.

Where the upstream primer is used in the step (a), the conditions for cleavage of the PTO may comprise extension reaction of the upstream primer.

According to an embodiment, the upstream primer is used in the step (a), a template-dependent polymerase is used for extension of the upstream primer and the template-dependent polymerase is identical to the enzyme having the 5' nuclease activity.

Optionally, the upstream primer is used in the step (a), a template-dependent polymerase is used for extension of the upstream primer and the template-dependent polymerase is different from the enzyme having the 5' nuclease activity.

Step (c): Hybridization of the Fragment Released from the PTO with hCTO

The fragment released from the PTO is hybridized with a hCTO (hybridizing-capturing and templating oligonucleotide).

The hCTO comprises (i) a CTO in a 3' to 5' direction comprising a capturing portion comprising a nucleotide sequence complementary to the 5'-tagging portion or a part of the 5'-tagging portion of the PTO and a templating portion comprising a nucleotide sequence non-complementary to the 5'-tagging portion and the 3'-targeting portion of the PTO, and (ii) at the 3'- or 5'-end of the CTO an IO-hybridizing portion comprising a nucleotide sequence complementary to an immobilized oligonucleotide (IO) immobilized on a solid substrate. The IO-hybridizing portion is located at either the 3'- or 5'-end of the hCTO.

The CTO as a basic structure in the hCTO has the following portions and functions:

The CTO is acted as a template for extension of the fragment released from the PTO. The fragment serving as a primer is hybridized with the CTO and extended to form an extended duplex.

The templating portion may comprise any sequence so long as it is non-complementary to the 5'-tagging portion and the 3'-targeting portion of the PTO. Furthermore, the templating portion may comprise any sequence so long as it can be acted as a template for extension of the fragment released from the PTO.

As described above, when the fragment having the 5'-tagging portion of the PTO is released by the cleavage reaction, the capturing portion of the CTO may be designed to comprise a nucleotide sequence complementary to the 5'-tagging portion. When the fragment having the 5'-tagging portion and a 5'-end part of the 3'-targeting portion is released, the capturing portion of the CTO may be designed to comprise a nucleotide sequence complementary to the 5'-tagging portion and the 5'-end part of the 3'-targeting portion. When the fragment having a part of the 5'-tagging portion of the PTO is released, the capturing portion of the CTO may be designed to comprise a nucleotide sequence complementary to the part of the 5'-tagging portion.

Moreover, it is possible to design the capturing portion of the CTO with anticipating cleavage sites of the PTO. For example, where the capturing portion of the CTO is designed to comprise a nucleotide sequence complementary to the 5'-tagging portion, either the fragment having a part of the 5'-tagging portion or the fragment having the 5'-tagging portion can be hybridized with the capturing portion and then extended. Where the fragment comprising the 5'-tagging portion and a 5'-end part of the 3'-targeting portion is released, it may be hybridized with the capturing portion of the CTO designed to comprise a nucleotide sequence complementary to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-3 mismatch nucleotides).

Figure 1B:
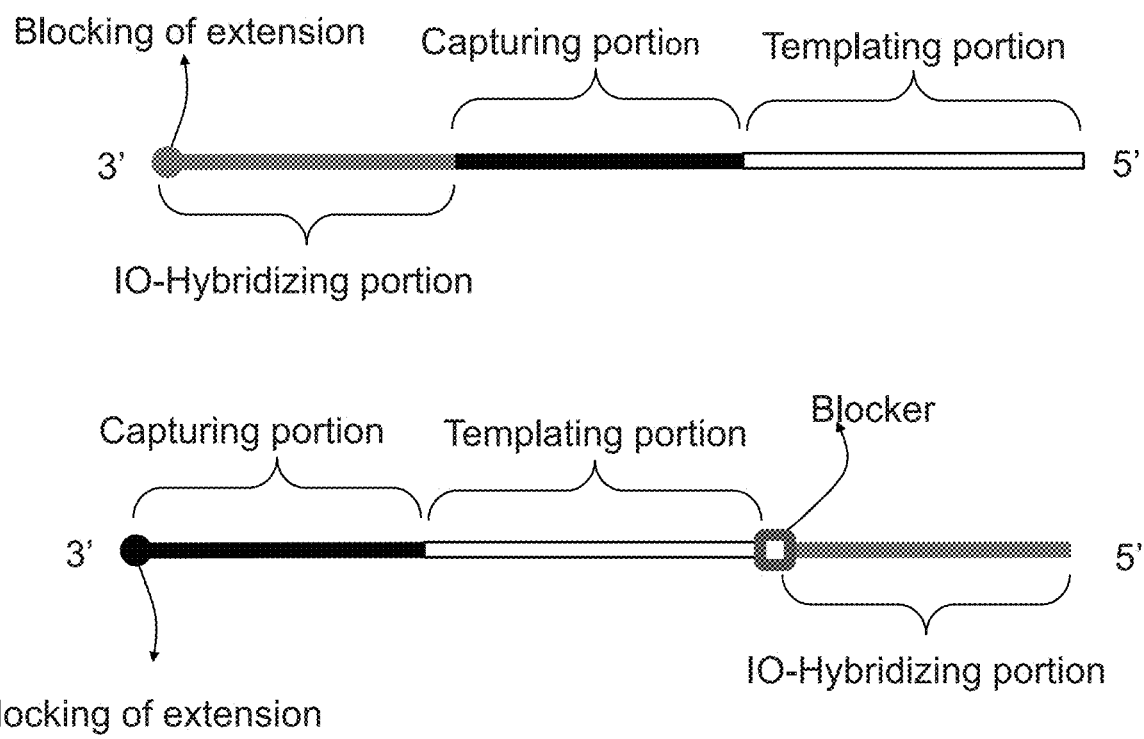
Figure 1C:
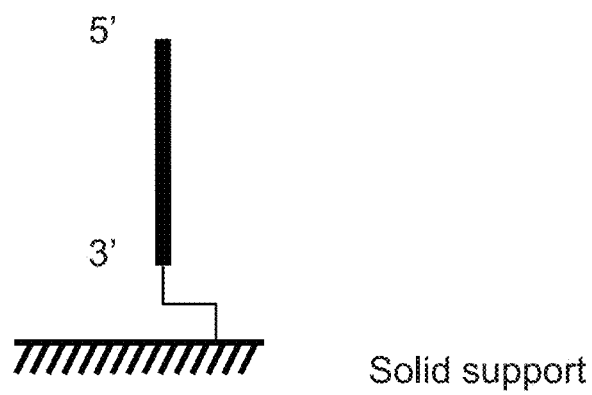
Figure 1C:
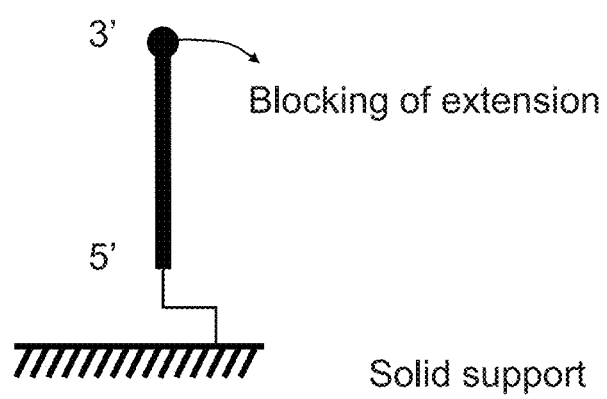

When the fragment comprising the 5'-tagging portion and a 5'-end part of the 3'-targeting portion is released, the 5'-end part of the capturing portion of the CTO (see FIG. 1B) may be designed to have a nucleotide sequence complementary to the cleaved 5'-end part of the 3'-targeting portion, overcoming problems associated with mismatch nucleotides.

In an embodiment, the nucleotide sequence of the 5'-end part of the capturing portion of the CTO complementary to the cleaved 5'-end part of the 3'-targeting portion may be selected depending on anticipated cleavage sites on the 3'-targeting portion of the PTO. The nucleotide sequence of the 5'-end part of the capturing portion of the CTO complementary to the cleaved 5'-end part of the 3'-targeting portion may be 1-10 nucleotides, 1-5 nucleotides or 1-3 nucleotides in length.

The 3'-end of the CTO may comprise additional nucleotides not involved in hybridization with the fragment. Moreover, the capturing portion of the CTO may comprise a nucleotide sequence complementary only to a part of the fragment (e.g., a part of the fragment containing its 3'-end portion) so long as it is stably hybridized with the fragment.

The term used "capturing portion comprising a nucleotide sequence complementary to the 5'-tagging portion or a part of the 5'-tagging portion" is described herein to encompass various designs and compositions of the capturing portion of the CTO as discussed above.

The CTO may be designed to have a hairpin structure.

The length of the CTO may be widely varied. For example, the CTO is 6-1000 nucleotides, 6-500 nucleotides, 6-300 nucleotides, 6-100 nucleotides, 6-80 nucleotides, 6-60 nucleotides, 6-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length. The capturing portion of the CTO may have any length so long as it is specifically hybridized with the fragment released from the PTO. For example, the capturing portion of the CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length. The templating portion of the CTO may have any length so long as it can act as a template in extension of the fragment released from the PTO. For example, the templating portion of the CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the CTO may have a 3'-OH terminal. Specifically, the 3'-end of the CTO is blocked to prohibit its extension. The non-extendible blocking of the CTO may be achieved in accordance with conventional methods. For instance, the blocking may be performed by adding to the 3'-hydroxyl group of the last nucleotide of the CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The fragment released from the PTO is hybridized with the capturing portion of the CTO, providing a form suitable in extension of the fragment. Although an undigested PTO is also hybridized with the capturing portion of the CTO through its 5'-tagging portion, its 3'-targeting portion is not hybridized to the CTO which prohibits the formation of an extended duplex.

The hybridization in the step (c) can be described in detail with referring to descriptions in the step (a).

The hCTO comprises an IO-hybridizing portion comprising a nucleotide sequence complementary to an immobilized oligonucleotide (IO) immobilized on a solid substrate.

The IO-hybridizing portion of the hCTO is a portion to remain in a single strand state when the extension of the fragment occurs on the hCTO.

According to an embodiment, the IO-hybridizing portion is linked to the 3'-end of the CTO. In such case, the hCTO comprises in a 3' to 5' direction the IO-hybridizing portion, the capturing portion and the templating portion. As the PTO fragment is hybridized with the capturing portion and then extended, the IO-hybridizing portion remains in a single strand state.

According to an embodiment, the IO-hybridizing portion is linked to the 5'-end of the CTO. In such case, the hCTO comprises in a 3' to 5' direction the capturing portion, the templating portion and the IO-hybridizing portion. In this embodiment, the IO-hybridizing portion may be involved in a double strand upon extending the PTO fragment hybridized with the capturing portion. According to an embodiment, when the IO-hybridizing portion is located at the 5'-end of the CTO, the hCTO further comprises a blocker portion between the CTO and the IO-hybridizing portion to prevent extension reaction of the fragment.

Where the hCTO is prepared by linking the 5'-end of the templating portion to the 5'-end of the IO-hybridizing portion, the requirement for the blocker may be avoided.

The IO-hybridizing portion may have any length. For example, the IO-hybridizing portion is 5-1000 nucleotides, 5-500 nucleotides, 5-300 nucleotides, 5-100 nucleotides, 5-80 nucleotides, 5-60 nucleotides, 5-40 nucleotides, 10-1000 nucleotides, 10-500 nucleotides, 10-300 nucleotides, 10-100 nucleotides, 10-80 nucleotides, 10-60 nucleotides, 10-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length.

The blocker located between the CTO and the IO-hybridizing portion and capable of preventing action of a template-dependent nucleic acid polymerase on synthesis of the opposite strand may include any blocker suitable in preventing such action of a template-dependent nucleic acid polymerase. For example, the blocker may include compounds containing alkylene groups, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage or aryl phosphoroamidate linkage. In an embodiment, carbon spacers may be used as blockers.

The IO-hybridizing portion of the hCTO comprises a nucleotide sequence complementary to an immobilized oligonucleotide (IO) immobilized on a solid substrate. The hCTO is very effectively hybridized with the IO immobilized on a solid substrate because the IO-hybridizing portion maintains its single strand state.

The 3'-end of the hCTO may have a 3'-OH terminal. In certain embodiment, the 3'-end of the hCTO is "blocked" to prohibit its extension.

Step (d): Extension of the Fragment to Form Extended Duplex Containing a Single Strand Portion The extension reaction is carried out using the resultant of the step (c) and a template-dependent nucleic acid polymerase. The fragment hybridized with the capturing portion of the hCTO is extended to form an extended strand complementary to the templating portion of the hCTO, thereby forming the extended duplex. The IO-hybridizing portion remains in a single strand state. As result, the extended duplex containing a single strand portion is formed.

In contrast, uncleaved PTO hybridized with the capturing portion of the hCTO is not extended such that no extended duplex is formed.

The term used herein "extended duplex" means a duplex formed by extension reaction in which the fragment hybridized with the capturing portion of the hCTO is extended using the templating portion of the hCTO as a template and the template-dependent nucleic acid polymerase.

The term used herein "extended strand" in conjunction with the fragment means a sequence composed of the fragment and its extended sequence.

The term used herein "extended sequence" in conjunction with the fragment means only a newly extended sequence which is a portion of the extended strand except the fragment.

The extended duplex formed by using the hCTO as templates may be described as either "hCTO-extended duplex" or "extended duplex hCTO".

The hCTO-extended duplex or extended duplex hCTO is a hybridization resultant of the hCTO and the extended strand.

The extended duplex may be rendered to have different $T_m$ value from that of the hybrid between the uncleaved PTO and the hCTO.

In an embodiment, the extended duplex has higher $T_m$ value than the hybrid between the uncleaved PTO and the hCTO.

The $T_m$ value of the extended duplex is adjustable by (i) a sequence and/or length of the fragment, (ii) a sequence and/or length of the hCTO or (iii) the sequence and/or length of the fragment and the sequence and/or length of the hCTO. Particularly, the $T_m$ value of the extended duplex is adjustable by a sequence and/or length of the CTO as a basic structure of the hCTO.

It is a technical feature of the present invention that the adjustable $T_m$ value of the extended duplex is employed to give a target signal indicative of the presence of the extended duplex.

The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$ value may be calculated by conventional methods such as Wallace rule (R. B. Wallace, et al., *Nucleic Acids Research*, 6:3543-3547(1979)) and nearest-neighbor method (SantaLucia J. Jr., et al., *Biochemistry*, 35:3555-3562(1996)); Sugimoto N., et al., *Nucleic Acids Res.*, 24:4501-4505(1996)).

According to an embodiment, the $T_m$ value refers to actual $T_m$ values under reaction conditions actually practiced.

The template-dependent nucleic acid polymerase used in the step (d) may include any nucleic acid polymerases, for example, Klenow fragment of *E. coli* DNA polymerase I, a thermostable DNA polymerase and bacteriophage T7 DNA polymerase.

Specifically, the polymerase is a thermostable DNA polymerase which may be obtained from a variety of bacterial species, including *Thermus aquaticus* (Taq), *Thermus thermophilus* (Tth), *Thermus filiformis*, *Thermis flavus*, *Thermococcus literalis*, *Thermus antranikiani*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosipho africanus*, *Pyrococcus furiosus*(Pfu), *Pyrococcus woesei*, *Pyrococcus horikoshii*, *Pyrococcus abyssi*, *Pyrodictium occultum*, *Aquifex pyrophilus* and *Aquifex aeolieus*. More specifically, the template-dependent nucleic acid polymerase is Taq polymerase.

According to an embodiment, the enzyme having the 5' nuclease activity used in the step (b) is identical to the template-dependent nucleic acid polymerase used in the step (d). Specifically, the enzyme having the 5' nuclease activity used in the step (b), the template-dependent nucleic acid polymerase used for extension of the upstream primer and the template-dependent nucleic acid polymerase used in the step (d) are identical to one another.

The step (d) is performed under conditions such that the fragment hybridized with the capturing portion of the hCTO is extended to produce the extended strand complementary to the templating portion of the hCTO and the extended duplex is formed.

Step (e): Hybridization Between Extended Duplex and IO

Afterwards, the resultant of the step (d) is hybridized with an immobilized oligonucleotide (IO) on a solid substrate.

The IO is immobilized onto a solid substrate and comprises a nucleotide sequence complementary to the IO-hybridizing portion of the hCTO. The IO is hybridized with the IO-hybridizing portion of the hCTO to form an IO duplex.

The term used herein "IO duplex" refers to a duplex formed by hybridization between the IO and the IO-hybridizing portion of the hCTO.

The IO duplex includes not only the hybrid between the IO and the hCTO involved in the extended duplex (i.e., hCTO-extended duplex) but also the hybrid between the IO and the hCTO not involved in the extended duplex.

Where the target nucleic acid sequence is present in a nucleic acid sample to be analyzed, the extended duplex is formed on the hCTO working as templates and hybridized with the IO through the IO-hybridizing portion of the hCTO in the extended duplex. While the extended duplex is formed on the hCTO, the IO-hybridizing portion remains in a single strand state, ensuring effective hybridization between the extended duplex and the IO.

Where the target nucleic acid sequence is absent in a nucleic acid sample, the extended duplex is not formed and the IO is hybridized with a bare hCTO not containing the extended strand.

According to an embodiment of the present invention, the hCTO forming the hCTO-extended duplex with the extended strand is hybridized with the IO.

Alternatively, according to an embodiment of the present invention, before the hCTO extended duplex is hybridized with the IO, the steps for dissociating the hCTO-extended duplex into the hCTO and the extended strand, hybridizing the hCTO with the IO and hybridizing the extended strand with the hCTO hybridized with the IO, thereby obtaining the hybrid between the hCTO-extended duplex and the IO.

The IO may have any length so long as it is specifically hybridized with the IO-hybridizing portion of the hCTO. For example, the IO is 5-1000 nucleotides, 5-500 nucleotides, 5-300 nucleotides, 5-100 nucleotides, 5-80 nucleotides, 5-60 nucleotides, 5-40 nucleotides, 10-1000 nucleotides, 10-500 nucleotides, 10-300 nucleotides, 10-100 nucleotides, 10-80 nucleotides, 10-60 nucleotides, 10-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length.

The sequence and length of the IO and the IO-hybridizing portion of the hCTO may be predetermined such that a duplex between the IO and the IO-hybridizing portion of the hCTO is maintained under conditions for detection of the presence of the extended duplex on a solid phase.

The 3'-end of the IO may have a 3'-OH terminal. In certain embodiment, the 3'-end of the IO is blocked to prohibit its extension.

Where the extension of the PTO fragment on the hCTO is performed in the presence of the IO, some of the hCTOs are likely to be hybridized with the IO before the formation of the extended duplex, resulting in occurrence of some extension reactions on a solid phase. Meanwhile, the extension reaction on the hCTO present in a liquid phase is more effective than the solid phase extension.

In certain embodiment, the present invention is performed with adjusting reaction conditions such that the hCTO is not hybridized with the IO before the formation of the extended duplex but after the extension reaction of the PTO fragment on the hCTO, the extension result is hybridized with IO. For example, either the sequences of the oligonucleotides used in the present invention or reaction conditions (e.g., temperature) are selected or adjusted such that the hybridization and extension of the PTO fragment may be undertaken under more stringent conditions than those for the hybridization between the IO and the IO-hybridizing portion.

In certain embodiment, the formation of the extended duplex and the hybridization with the IO are carried out in different tubes from each other, thereby preventing hybridization of the hCTO with the IO on a solid phase before the extension reaction.

Whether the hCTO involved in the extended duplex or the bare hCTO not involved in the extended duplex is hybridized with the IO may be determined by detecting signals provided on a solid phase.

The extended duplex provides a target signal by (i) at least one label linked to the fragment and/or the hCTO, (ii) a label incorporated into the extended duplex during the extension reaction, (iii) a label incorporated into the extended duplex during the extension reaction and a label linked to the fragment and/or the hCTO, or (iv) a label linked to the fragment or incorporated into the extended duplex during the extension reaction and a label linked to the IO; and Since the extended duplex is formed only when the target nucleic acid sequence is present, its presence indicates the presence of the target nucleic acid sequence.

The term used herein "target signal" means any signal capable of indicating the presence of the extended duplex. For example, the target signal includes a signal from labels (signal generation or extinguishment) and a signal change from labels (signal increase or decrease).

Some of labeling systems to give the target signal may provide signals upon the formation of the hybrid between uncleaved PTO and the hCTO, which have identical characteristics to the target signal. The signal generated upon the formation of the hybrid between uncleaved PTO and the hCTO is described as "non-target signal". The non-target signal may be removed by using $T_m$ difference between the extended duplex and the hybrid of uncleaved PTO and the hCTO (see WO 2012/096523). The $T_m$ value of the extended duplex may be arbitrarily adjusted. In certain embodiment, the $T_m$ value of the extended duplex may be adjusted to be higher than that of the hybrid between uncleaved PTO and the hCTO. Given that the target signal is detected at a pre-determined temperature at which the extended duplex is in a double strand state, the $T_m$ value of the hybrid between uncleaved PTO and the hCTO may be adjusted such that the hybrid between uncleaved PTO and the hCTO is dissociated at the pre-determined temperature, thereby removing the non-target signal. In certain embodiment, a signal from a negative control containing no target sequence may be employed as a reference.

The labeling systems used in this invention may be described as follows:

(i) At Least One Label Linked to the Fragment and/or the hCTO

In certain embodiment, the target signal is provided at least one label linked to the fragment and/or the hCTO. The extended duplex is formed between the PTO fragment and the hCTO and the label linked to the fragment and/or the hCTO is present in the extended duplex, thereby providing the target signal.

The label includes an interactive dual label and a single label.

(i-1) Interactive Dual Label

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively. Interactive dual label includes the label pair providing detectable signal based on contact-mediated quenching (Salvatore et al., Nucleic Acids Research, 2002 (30) no. 21 e122 and Johansson et al., J. AM. CHEM. SOC 2002 (124) pp 6950-6956). In the present invention, the interactive label system includes any or all cases inducing signal changes by interaction between at least two molecules (e.g. dyes).

In an embodiment of the interactive dual label system, the hCTO has an interactive dual label comprising a reporter molecule and a quencher molecule; the extension of the fragment in the step (d) induces change of a signal from the interactive dual label to give the target signal. In an embodiment, the reporter molecule and the quencher molecule on the hCTO are positioned at a site such that change of a signal from the interactive dual label is induced by the extension of the fragment in the step (d). In an embodiment, the reporter molecule and the quencher molecule are positioned on the templating portion of the hCTO. Where the reporter molecule and the quencher molecule are positioned on the templating portion of the hCTO and the templating portion is in a single strand state, the reporter molecule and the quencher molecule are conformationally adjacent to each other to allow the quencher molecule to quench the signal from the reporter molecule. Upon the formation of the extended duplex in the step (d), the reporter molecule and the quencher molecule on the hCTO are conformationally separated to allow the quencher molecule to unquench the signal from the reporter molecule, thereby providing the target signal. The detection of the target signal provided from the extended duplex hybridized with the IO immobilized on a solid phase allows for determining the presence of the extended duplex.

The expression used herein "the reporter molecule and the quencher molecule are conformationally adjacent" means that the reporter molecule and the quencher molecule are three-dimensionally adjacent to each other by a conformational structure of a label-bearing strand (e.g., the fragment or hCTO) such as random coil and hairpin structure.

The expression used herein "the reporter molecule and the quencher molecule are conformationally separated" means that the reporter molecule and the quencher molecule are three-dimensionally separated by change of a conformational structure of a label-bearing strand (e.g., the fragment or hCTO) upon the formation of a double strand.

In another embodiment of the interactive dual label system, the hCTO has an interactive dual label comprising a reporter molecule and a quencher molecule; wherein the hybridization of the fragment with the hCTO in the step (c) induces change of a signal from the interactive dual label to give the target signal and the extended duplex maintains the target signal. In an embodiment, the reporter molecule and the quencher molecule on the hCTO are positioned at a site such that change of a signal from the interactive dual label is induced by the hybridization of the fragment with the hCTO in the step (c). In an embodiment, the reporter molecule and the quencher molecule are positioned on the capturing portion of the hCTO. Where the reporter molecule and the quencher molecule are positioned on the capturing portion of the hCTO and the capturing portion is in a single strand state, the reporter molecule and the quencher molecule are conformationally adjacent to each other to allow the quencher molecule to quench the signal from the reporter molecule. Upon hybridizing the fragment with the capturing portion of the hCTO, the reporter molecule and the quencher molecule on the hCTO are conformationally separated to allow the quencher molecule to unquench the signal from the reporter molecule, thereby providing the target signal. The extended duplex permits to maintain the target signal. The detection of the target signal provided from the extended duplex hybridized with the IO immobilized on a solid phase allows for determining the presence of the extended duplex. In such embodiment, the hybrid between the uncleaved PTO and the hCTO may provide a non-target signal. The non-target signal may be removed by adjustment of detection temperatures using $T_m$ difference between the extended duplex and the hybrid of uncleaved PTO and the hCTO.

In another embodiment of the interactive dual label system, the fragment has an interactive dual label comprising a reporter molecule and a quencher molecule; wherein the hybridization of the fragment with the hCTO in the step (c) induces change of a signal from the interactive dual label to give the target signal and the extended duplex maintains the target signal. In an embodiment, the reporter molecule and the quencher molecule on the PTO fragment are positioned at a site such that change of a signal from the interactive dual label is induced by the hybridization of the fragment with the hCTO in the step (c). In an embodiment, the reporter molecule and the quencher molecule are positioned on the 5'-tagging portion of the PTO fragment. Where the reporter molecule and the quencher molecule are positioned on the PTO fragment and the PTO fragment (or the 5'-tagging portion) is in a single strand state, the reporter molecule and the quencher molecule are conformationally adjacent to each other to allow the quencher molecule to quench the signal from the reporter molecule. Upon hybridizing the PTO fragment with the capturing portion of the hCTO, the PTO fragment is involved in a double strand and the reporter molecule and the quencher molecule are conformationally separated to allow the quencher molecule to unquench the signal from the reporter molecule, thereby providing the target signal. The extended duplex permits to maintain the target signal. The detection of the target signal provided from the extended duplex hybridized with the IO immobilized on a solid phase allows for determining the presence of the extended duplex. In such embodiment, the hybrid between the uncleaved PTO and the hCTO may provide a non-target signal. The non-target signal may be removed by adjustment of detection temperatures using $T_m$ difference between the extended duplex and the hybrid of uncleaved PTO and the hCTO.

According to an embodiment, where the interactive dual label is present on the same strand, the reporter molecule and the quencher molecule are separately positioned by at least 4 nucleotides, at least 7 nucleotides, at least 10 nucleotides, at least 15 nucleotides or at least 20 nucleotides.

In another embodiment of the interactive dual label system, the fragment has one of an interactive dual label comprising a reporter molecule and a quencher molecule and the hCTO has the other of the interactive dual label; wherein the hybridization of the fragment with the hCTO in the step (c) induces change of a signal from the interactive dual label to give the target signal and the extended duplex maintains the target signal. In such case, the interactive dual label may be located at sites such that change of a signal from the interactive dual label is induced by the hybridization of the fragment with the hCTO in the step (c). In an embodiment, one of the interactive dual label is located at the 5'-end of the PTO and the other is located at the 3'-end of the capturing portion of the hCTO. Where one of the interactive dual label is located at the 5'-end of the PTO and the other is located at the 3'-end of the capturing portion of the hCTO, the reporter molecule and the quencher molecule are separated before hybridization between the fragment and the hCTO such that the quencher molecule does not quench the signal from the reporter molecule. Where the fragment is hybridized with the capturing portion of the hCTO in the step (c), the reporter molecule and the quencher molecule are adjacent to each other to allow the quencher molecule to quench the signal from the reporter molecule, thereby providing the target signal. The extended duplex permits to maintain the target signal. The detection of the target signal provided from the extended duplex hybridized with the IO immobilized on a solid phase allows for determining the presence of the extended duplex. In such embodiment, the hybrid between the uncleaved PTO and the hCTO may provide a non-target signal. The non-target signal may be removed by adjustment of detection temperatures using $T_m$ difference between the extended duplex and the hybrid of uncleaved PTO and the hCTO.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DiIC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. R, Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent black quencher molecule (or dark quencher molecule) capable of quenching a fluorescence of a wide range of wavelengths or a specific wavelength may be used in the present invention. Examples of those are BHQ and DABCYL.

In accordance with the types of the interactive dual label systems, signal from either the reporter molecule or the quencher molecule may be detected.

In the FRET label, the reporter encompasses a donor of FRET and the quencher encompasses the other partner (acceptor) of FRET. For example, a fluorescein dye is used as the reporter and a rhodamine dye as the quencher.

(i-2) Single Label

In an embodiment of the single label, the hCTO has a single label and the extension of the fragment in the step (d) induces change of a signal from the single label to give the target signal. In an embodiment, the single label on the hCTO is positioned at a site such that change of a signal from the single label is induced by the extension of the fragment in the step (d). In an embodiment, the single label is positioned on the templating portion of the hCTO. In an embodiment, the single label capable of providing a different signal depending on its presence on a double strand or single strand is useful in the present invention, because the present invention comprises hybridizing the hCTO with the IO. Any single label may be used so long as it has characteristics described above. Exemplified single fluorescent labels with the above-described characteristics are disclosed U.S. Pat. Nos. 7,537,886 and 7,348,141 which describe types and preferable linking sites of single fluorescent labels. In an embodiment, the single fluorescent label includes JOE, FAM, TAMRA, ROX and fluorescein-based label. In an embodiment, the labeled nucleotide residue may be positioned at internal nucleotide residue within the oligonucleotide rather than at the 5'-end or the 3'-end.

Where such single fluorescent label is positioned on the templating portion of the hCTO and the extended duplex is formed in the step (d), the templating portion of the hCTO becomes in a double strand state and the fluorescent signal intensity from the single label becomes increased compared with that from the single label in a single strand state. Therefore, in embodiments using the single label, the detection of signal increase on a solid phase allows for determining the presence of the extended duplex.

In another embodiment of the single label, the hCTO has a single label and the hybridization of the fragment with the hCTO in the step (c) induces change of a signal from the single label to give the target signal and the extended duplex maintains the target signal. In an embodiment, the single label on the hCTO is positioned at a site such that change of a signal from the single label is induced by the hybridization of the fragment with the hCTO in the step (c). In an embodiment, the single label is positioned on the capturing portion of the hCTO. The extended duplex permits to maintain the target signal. Therefore, in embodiments using the single label, the detection of signal increase on a solid phase allows for determining the presence of the extended duplex.

In an embodiment, the single label capable of providing a different signal depending on its presence on a double strand or single strand is used. Where such single fluorescent label is positioned on the capturing portion of the hCTO and the fragment is hybridized with the capturing portion of the hCTO in the step (c), the capturing portion of the hCTO becomes in a double strand state and the fluorescent signal intensity from the single label becomes increased compared with that from the single label in a single strand state.

Therefore, in embodiments using the single label, the detection of signal increase on a solid phase allows for determining the presence of the extended duplex. In an embodiment, the non-target signal may be provided by the hybrid of uncleaved PTO and the hCTO and may be removed by adjustment of detection temperatures using $T_m$ difference between the extended duplex and the hybrid of uncleaved PTO and the hCTO.

In still another embodiment of the single label, the fragment has a single label, the hybridization between the fragment and the hCTO in the step (c) provides the target signal and the extended duplex maintains the target signal.

The single label linked to the fragment includes any signal label capable of providing a signal indicative of the extended duplex on a solid phase, for example, a fluorescent label, a luminescent label, a chemiluminescent label, an electrochemical label, a metal label, a chemical label (e.g., biotin) and enzymatic label (e.g., alkaline phosphatase, peroxidase, Q-galactosidase and R-gluocosidase). The single fluorescent label useful in the present invention may be described with reference to descriptions for reporter and quencher molecules as indicated above.

FIGS. 2A-2D illustrate an embodiment using the PTO fragment with a single label.

Where the fluorescent single label is positioned on the PTO fragment and the PTO fragment is hybridized with the capturing portion of the hCTO in the step (c), the single label linked to the PTO fragment provides the target signal and the extended duplex maintains the target signal. The detection of the target signal from the extended duplex hybridized with the IO immobilized on a solid phase allows for determining the presence of the extended duplex. In an embodiment, the non-target signal may be provided by the hybrid of uncleaved PTO and the hCTO and may be removed by adjustment of detection temperatures using $T_m$ difference between the extended duplex and the hybrid of uncleaved PTO and the hCTO.

(ii) Label Incorporated into Extended Duplex

The present invention may use a label incorporated into extended duplex for providing the target signal indicative of the presence of the extended duplex.

In an embodiment using the label incorporated during the extension reaction, the target signal is provided by a single label incorporated into the extended duplex during the extension reaction and the incorporated single label is linked to a nucleotide incorporated during the extension reaction.

In certain embodiment, a plurality of the same single labels may be incorporated. The single label may include any label as long as it is capable of providing a signal indicative of the extended duplex on a solid phase.

FIGS. 3A-3D illustrate an embodiment using the label incorporated during the extension reaction. When the PTO fragment is extended on the hCTO and a nucleotide with a label is incorporated. The label incorporated into the extended duplex provides the target signal. The detection of the target signal from the extended duplex hybridized with the IO immobilized on a solid phase allows for determining the presence of the extended duplex.

In an embodiment, the nucleotide incorporated during the extension reaction has a first non-natural base and the hCTO has a nucleotide having a second non-natural base with a specific binding affinity to the first non-natural base. In an embodiment, the nucleotide having the second non-natural base may be located on any site of the templating portion of the hCTO. In an embodiment, the non-natural base is used to incorporate a label into a certain site.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns (e.g., hydrogen bond patterns) from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner. Specific examples of non-natural bases include the following bases in base pair combinations: iso-C/iso-G, iso-dC/iso-dG, K/X, H/J, and M/N (see U.S. Pat. No. 7,422,850).

FIGS. 3A-3D illustrate an embodiment using a non-natural base to incorporate a label into a certain site. The fragment is hybridized with the hCTO containing a nucleotide having the second non-natural base (e.g., iso-dC) with a specific binding affinity to the first non-natural base (e.g., iso-dG). The extension reaction is carried out in the presence of a nucleotide having the first non-natural base with a fluorescent single label, thereby forming the extended duplex. In the extension reaction, the nucleotide having the first non-natural base is incorporated into a site opposite to the nucleotide having the second non-natural base. The detection of the target signal from the extended duplex hybridized with the IO immobilized on a solid phase allows for determining the presence of the extended duplex.

The types and properties of the single label used may be described with descriptions of label systems for "labels linked to fragment and hCTO" described above.

(iii) Combination of Label Incorporated into Extended Duplex and Label Linked to Fragment and/or hCTO In an embodiment using the label incorporated into extended duplex during the extension reaction and the label linked to fragment and/or hCTO, the target signal is provided by the label incorporated into the extended duplex during the extension reaction and the label linked to the fragment and/or the hCTO; wherein the label incorporated is linked to a nucleotide incorporated during the extension reaction; wherein the two labels are an interactive dual label of a reporter molecule and a quencher molecule; wherein the extension of the fragment in the step (d) induces change of a signal from the interactive dual label to give the target signal.

In an embodiment, the incorporated label and the label linked to fragment and/or hCTO are positioned at a site such that change of a signal from the interactive dual label is induced by the extension of the fragment in the step (d).

In certain embodiment, the nucleotide incorporated during the extension reaction has a first non-natural base and the hCTO has a nucleotide having a second non-natural base with a specific binding affinity to the first non-natural base.

In an embodiment, the non-natural base is used to incorporate a label into a certain site.

In an embodiment, the fragment is hybridized with the hCTO containing at the 5'-end of the templating portion (i) a nucleotide having the second non-natural base (e.g., iso-dC) with a specific binding affinity to the first non-natural base (e.g., iso-dG) and (ii) a reporter. The extension reaction is carried out in the presence of a nucleotide having the first non-natural base with a quencher molecule, thereby forming the extended duplex and quenching a signal from the reporter molecule by the quencher molecule. In other words, the extension of the fragment in the step (d) induces change of a signal from the interactive dual label to give the target signal. In the extension reaction, the nucleotide having the first non-natural base is incorporated into a site opposite to the nucleotide having the second non-natural base. The detection of the target signal from the extended duplex hybridized with the IO immobilized on a solid phase allows for determining the presence of the extended duplex.

In certain embodiment, the quencher molecule is linked to the hCTO and the reporter molecule is incorporated during the extension reaction.

In another embodiment, the fragment with a reporter is hybridized with the hCTO containing in the templating portion a nucleotide having the second non-natural base (e.g., iso-dC) with a specific binding affinity to the first non-natural base (e.g., iso-dG). The extension reaction is carried out in the presence of a nucleotide having the first non-natural base with a quencher molecule, thereby forming the extended duplex and quenching a signal from the reporter molecule by the quencher molecule. In other words, the extension of the fragment induces change of a signal from the interactive dual label to give the target signal indicative of the presence of the extended duplex. The position into which the quencher molecule is incorporated includes any position such that the quencher molecule quenches the signal from the reporter molecule in the extended duplex.

In certain embodiment, the quencher molecule is linked to the fragment and the reporter molecule is incorporated during the extension reaction.

The detection of the target signal from the extended duplex hybridized with the IO immobilized on a solid phase allows for determining the presence of the extended duplex.

(iv) Combination of Label Linked to the Fragment or Incorporated into the Extended Duplex and Label Linked to IO In an embodiment using the label linked to the fragment or incorporated into the extended duplex during the extension reaction and the label linked to the IO, the target signal is provided by the label linked to the fragment or incorporated into the extended duplex during the extension reaction and the label linked to the IO; the label linked to the fragment or incorporated into the extended duplex during the extension reaction has one of an interactive dual label comprising a reporter molecule and a quencher molecule and the IO has the other of the interactive dual label; wherein the hybridization of the IO with the extended duplex in the step (e) induces change of a signal from the interactive dual label to give the target signal.

The target signal is provided only when the extended duplex is hybridized with the IO.

In an embodiment, the label linked to the fragment or incorporated into the extended duplex and the label linked to the IO are positioned at sites such that change of a signal from the interactive dual label is induced by the hybridization of the IO with the extended duplex in the step (e).

In an embodiment, the IO-hybridizing portion in the hCTO is located at the 3'-end of the CTO as the basic structure of the hCTO, the IO is immobilized on a solid phase through its 5'-end, the quencher molecule is linked to the 5'-end of the PTO fragment and the reporter molecule to the 3'-end of the IO. Where the PTO fragment with the quencher molecule at its 5'-end is hybridized with the hCTO, the extended duplex is formed, and the extended duplex is hybridized with the IO, the quencher molecule on the extended duplex and the reporter molecule on the IO are adjacent to each other, thereby inducing change of a signal from the interactive dual label.

In certain embodiment, the reporter molecule is linked to the PTO fragment and the quencher molecule to the IO.

The detection of the target signal provided from the extended duplex hybridized with the IO immobilized on a solid phase allows for determining the presence of the extended duplex.

In an embodiment, the non-target signal may be provided upon hybridization between the IO and the hybrid of uncleaved PTO/hCTO. The non-target signal may be removed by adjustment of detection temperatures at which the hybridization between the hCTO and the IO is maintained and the hybridization between the uncleaved PTO and the hCTO is dissociated.

In another embodiment, the IO-hybridizing portion in the hCTO is located at the 5'-end of the CTO as the basic structure of the hCTO, through a blocker and the IO is immobilized on a solid phase through its 3'-end. The quencher molecule is incorporated into the 3'-end of the extended strand of the PTO fragment during the extension reaction and the reporter molecule is linked to the 5'-end of the IO. Where the extended duplex containing the incorporated quencher into the 3'-end of the extended strand is formed and the extended duplex is hybridized with the IO, the quencher molecule on the extended duplex and the reporter molecule on the IO are adjacent to each other, thereby inducing change of a signal from the interactive dual label.

In certain embodiment, the reporter molecule is incorporated during the extension reaction and the quencher molecule is linked to the IO.

The detection of the target signal provided from the extended duplex hybridized with the IO immobilized on a solid phase allows for determining the presence of the extended duplex.

In an embodiment, the nucleotide incorporated during the extension reaction has a first non-natural base and the hCTO has a nucleotide having a second non-natural base with a specific binding affinity to the first non-natural base.

In an embodiment, the non-natural base is used to incorporate a label into a certain site.

The IO is directly or indirectly immobilized through its 5'-end or 3'-end onto a solid substrate. In an embodiment, the IO is immobilized through its 5'-end or 3'-end onto a solid substrate. Specifically, the IO is immobilized through its 3'-end onto a solid substrate.

The IO may be immobilized on the surface of the solid substrate in a covalent or non-covalent manner. Where the immobilized IOs are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for IO immobilization. In addition, poly (T) tail or poly (A) tail may serve as linkers. The poly (T) tail or poly (A) tail as linkers is not considered as a sequence of the IO.

According to an embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized IOs on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, Si/SiO$_2$ wafer, germanium, gallium arsenide, carbon, carbon nanotube, polymers (e.g., polystyrene, polyethylene, polypropylene and polyacrylamide), sepharose, agarose and colloids. The solid substrate may be in the form of a dipstick, a plate, a particle (e.g., bead), an affinity column and a membrane. A plurality of immobilized IOs in this invention may be immobilized on an addressable region or two or more addressable regions on a solid substrate that may comprise 2-1,000,000 addressable regions. Immobilized IOs may be fabricated to produce array or arrays for a given application by conventional fabrication technologies such as photolithography, ink-jetting, mechanical microspotting, and derivatives thereof.

The present invention performed on the solid phase can detect simultaneously a plurality of target nucleic acid sequences even using a single type of a label because immobilized IOs may be physically separated. In this regard, the number of target nucleic acid sequences to be detected by the present invention on the solid phase is not limited.

In an embodiment, the present invention further comprises the step of washing the solid phase (solid substrate). Even when washing the solid substrate is not performed, the signal may be detected on the solid substrate. For example, the signal only from solid substrate may be detected by using confocal microscopy without interference from signals from labels in a liquid phase.

Step (f): Detection of Target Signal

Finally, the extended duplex is detected on the solid phase by measuring the target signal, whereby the presence of the extended duplex indicates the presence of the target nucleic acid sequence.

Because the target signal is provided only when the extended duplex is maintained, the extended duplex is required at the time of signal detection to remain in a double strand state without dissociation. Because the extended duplex is bound to the IO through the IO-hybridizing portion of the hCTO, the IO and the IO-hybridizing portion are also required at the time of signal detection to remain in a double strand state.

Therefore, when the target signal is detected on the solid phase, a pre-determined temperature at which both the extended duplex and the IO duplex is in a double strand state is adopted.

Depending on the types of signaling systems, the non-target signal may be provided by hybridization between the 5'-tagging portion of uncleaved PTO and the hCTO (see FIGS. 2A-2D). In such case, the non-target signal may be removed by adjusting hybridization conditions.

As an example, the signal is detected at a pre-determined temperature at which both the extended duplex and the IO duplex remain in a double strand state and the hybrid between the uncleaved PTO and the hCTO is substantially dissociated.

The expression used herein with reference to detection temperatures of the extended duplex "temperature at which the hybrid between the uncleaved PTO and the hCTO is substantially dissociated" includes temperatures at which the hybrid between the uncleaved PTO and the hCTO is wholly or partially dissociated.

In an embodiment, the present invention may be carried out at temperatures at which the hybrid between the uncleaved PTO and the hCTO is even partially dissociated. In such case, a signal from a negative control containing no target sequence may be employed to verify whether a signal from a sample to be analyzed indicates the presence of the target nucleic acid sequence.

In an embodiment, the temperature for target detection is determined in considering $T_m$ values of the extended duplex, the IO duplex and/or the hybrid of the 5'-tagging portion of the uncleaved PTO and the hCTO.

In an embodiment, $T_m$ values of the extended duplex and the IO duplex are adjusted to be higher (e.g., at least 5° C. higher, at least 10° C. higher, at least 15° C. higher, at least 20° C. higher, at least 25° C. higher or at least 30° C. higher) than that of the hybrid of the 5'-tagging portion of the uncleaved PTO and the hCTO.

In an embodiment, the pre-determined temperature is higher than $T_m$ value of the hybrid of the uncleaved PTO and the hCTO minus 10° C. or 5° C. The pre-determined temperature may be higher than $T_m$ value of the hybrid of the uncleaved PTO and the hCTO. The pre-determined temperature may be higher than $T_m$ value of the hybrid of the uncleaved PTO and the hCTO plus 5° C.

The $T_m$ value of the extended duplex may be variously adjusted by (i) a sequence and/or length of the fragment, (ii) a sequence and/or length of the hCTO or (iii) the sequence and/or length of the fragment and the sequence and/or length of the hCTO. Also, the $T_m$ value of the IO duplex formed by hybridization between the IO and IO-hybridizing portion of the hCTO can be variously adjusted. Given such adjustment of $T_m$ values, a suitable temperature for dissociating the hybrid of the uncleaved PTO and the hCTO may be easily determined.

The primer, PTO, hCTO and IO may be comprised of naturally occurring dNMPs and/or NMPs. Alternatively, the primer, PTO, hCTO and IO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The primer, PTO, hCTO and IO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

As described above, the PTO may be cleaved at a site located in a 3'-direction apart from the 3'-end of the 5'-tagging portion of the PTO. The cleavage site may be located at the 5'-end part of the 3'-targeting portion of the PTO. Where the PTO fragment comprises the 5'-end part of the 3'-targeting portion of the PTO, a site of the hCTO hybridized with the 5'-end part of the 3'-targeting portion may comprise a universal base, degenerate sequence or their combination. For instance, if the PTO is cleaved at a site located one nucleotide in a 3'-direction apart from the 3'-end of the 5'-tagging portion of the PTO, it is advantageous that the 5'-end part of the capturing portion of the hCTO comprises a universal base for hybridization with the nucleotide. If the PTO is cleaved at a site located two nucleotides in a 3'-direction apart from the 3'-end of the 5'-tagging portion of the PTO, it is advantageous that the 5'-end of the capturing portion of the hCTO comprises a degenerate sequence and its 3'-direction-adjacent nucleotide comprises a universal base. As such, where the cleavage of the PTO occurs at various sites of the 5'-end part of the 3'-targeting portion, the utilization of universal bases and degenerate sequences in the hCTO is useful. In addition, where the PTOs having the same 5'-tagging portion are used for screening multiple target nucleic acid sequences under upstream primer extension-dependent cleavage induction, the PTO fragments having different 5'-end parts of the 3'-targeting portion may be generated. In such cases, universal bases and degenerate sequences are usefully employed in the hCTO. The strategies using universal bases and degenerate sequences in the hCTO ensure to use one type or minimal types of the hCTO for screening multiple target nucleic acid sequences.

According to an embodiment, the present method further comprises repeating all or some (e.g., steps (a)-(b), (a)-(d) or (a)-(e)) of the steps (a)-(f) with denaturation between repeating cycles. This repetition permits to amplify the target nucleic acid sequence and/or the target signal.

The denaturation may be carried out by conventional technologies, including, but not limited to, heating, alkali, formamide, urea and glyoxal treatment, enzymatic methods (e.g., helicase action), and binding proteins. For instance, the denaturation can be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

In certain embodiment, the cycle number of the repetition is adjusted to sufficiently cleave the PTO and to produce the extend strand in excessive amount.

According to an embodiment, the steps (a)-(f) are performed in a reaction vessel or in separate reaction vessels. For example, the steps (a)-(b), (c)-(d) and (e)-(f) are performed in different reaction vessels from one another.

In certain embodiment, the steps (a)-(b) and (c)-(f) are performed in a reaction vessel or in separate reaction vessels. The steps (a)-(b) and (c)-(f) may be carried out even in a reaction vessel in differential manner from each other. For example, where the hybridization between the 3'-targeting portion of the PTO and the target nucleic acid sequence may occur under higher stringent conditions unfavorable for the hybridization between the fragment and the hCTO, the repetition of the steps (a)-(b) may undertake with not accompanied by processing of the steps (c)-(f) and the steps (c)-(f) may undertake after completion of the steps (a)-(b).

In certain embodiment, the steps (a)-(d) and (e)-(f) are performed in two different reaction vessels from each other.

It would be obvious to one of skill in the art that the repetition of some steps, the intervention of the denaturation into the repetition, the separation of some step(s) and the detection time may be widely varied within the spirit of the invention.

In certain embodiment, where the repetition with denaturation between repeating cycles is carried out by using a reaction mixture of the step (a) containing an upstream primer, it is performed in the presence of a downstream primer, e.g., by PCR method.

In certain embodiment, where the repetition with denaturation between repeating cycles is carried out by using a reaction mixture of the step (a) containing an upstream probe, it is performed in the presence of a downstream primer.

The term used herein "nucleic acid sample" refers to a non-biological sample (e.g., food, water, air, soil and waste) or biological sample containing nucleic acid molecules. The biological sample may be derived from animal, plant, human, fungus, bacterium and virus. The biological sample may be cell, tissue, or fluid from a biological source, blood, plasma, serum, serum, plasma, lymph, milk, urine, faeces, ocular fluid, saliva, semen, brain extracts, spinal cord fluid, appendix, spleen and tonsillar tissue extracts.

The present invention does not require that target nucleic acid sequences to be detected and/or amplified have any particular sequence or length, including any DNA (gDNA and cDNA) and RNA molecules. The target nucleic acid sequence may be in a single- or double-strand.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer, an oligonucleotide dT primer hybridizable to poly A tail of mRNA or a target specific primer can be used.

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature. The target nucleic acid sequence may include known sequences.

The present invention is also useful in detection of a nucleotide variation. In certain embodiment, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic acid sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence. According to an embodiment, the 3'-end of the upstream primer has a complementary sequence to the nucleotide variation in a target nucleic acid sequence. The 3'-end of the upstream primer having a complementary sequence to the nucleotide variation in the target nucleic acid sequence is annealed to the matching template and extended to induce cleavage of the PTO. The resultant PTO fragment is hybridized with the hCTO, extended to form the extended duplex and IO-hybridizing portion of the hCTO is hybridized with the IO to provide the target signal on a solid substrate. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no generation of the extended duplex.

Alternatively, it is possible to use PTO cleavage depending on the hybridization of PTO having a complementary sequence to a nucleotide variation in a target nucleic acid sequence. For example, under controlled conditions, a PTO having a complementary sequence to the nucleotide variation in the target nucleic acid sequence is hybridized with the matching template and then cleaved. The resultant PTO fragment is hybridized with the hCTO, extended and hybridized with the IO to provide the target signal. While, under the controlled conditions, the PTO is not hybridized with a mismatching template having non-complementary sequence in the nucleotide variation position and not cleaved. Particularly, in this case, the complementary sequence to the nucleotide variation in the PTO is positioned at its middle of the 3'-targeting portion of the PTO.

According to an embodiment, the use of an artificial mismatch nucleotide enhances discrimination potential of the PTO to nucleotide variations.

Alternatively, the present invention uses the PTO having the nucleotide variation discrimination site positioned on the 5'-end part of the 3'-targeting portion for selectivity of the PTO to a specific nucleotide variation. The 5'-end part of the 3'-targeting portion of the PTO is positioned to a nucleotide variation in a target nucleic acid sequence for the detection of the nucleotide variation and the 5'-end part of the 3'-targeting portion of the PTO has a complementary sequence to the nucleotide variation in a target nucleic acid sequence.

Where the PTO is hybridized with the target nucleic acid sequence (i.e., match template) having the nucleotide variation complementary to the nucleotide variation discrimination site, the 5'-end part of the 3'-targeting portion forms a double strand with the match template; however, where the PTO is hybridized with a target nucleic acid sequence (i.e., mismatch template) having a nucleotide variation non-complementary to the nucleotide variation discrimination site, the 5'-end part of the 3'-targeting portion does not form a double strand with the mismatch template.

The term used herein "nucleotide variation discrimination site" with reference to the PTO is a complementary sequence on the 5'-end part of the 3'-targeting portion of the PTO to a nucleotide variation in a target nucleic acid sequence.

According to an embodiment, the nucleotide variation discrimination site is located within 10 nucleotides, more preferably 8 nucleotides, still more preferably 6 nucleotides, still much more preferably 4 nucleotides, 3 nucleotides, 2 nucleotides or 1 nucleotide apart from the 5'-end of the 3'-targeting portion of the PTO. Preferably, the nucleotide variation discrimination site is located at the 5'-end of the 3'-targeting portion of the PTO.

The term "site" with reference to either nucleotide variation discrimination site of probes or nucleotide variation site on target sequences is used herein to encompass not only a single nucleotide but also a plurality of nucleotides.

It is noteworthy that such distinct hybridization patterns on the nucleotide variation of interest are responsible for differences in initial cleavage sites of the PTO, thereby producing two types of PTO fragments to give signal differentiation depending on the presence of the nucleotide variation of interest.

In the presence of the nucleotide variation of interest, a first fragment is generated by cleavage of hybrid between the PTO and matching template, and in the absence of the nucleotide variation of interest, a second fragment is generate by cleavage of hybrid between the PTO and mismatching template. The second fragment comprises an additional 3'-end portion rendering the second fragment to be different from the first fragment.

In an embodiment for the detection of a single nucleotide variation, the 5'-end of the 3'-targeting portion of the PTO has a complementary sequence to the single nucleotide variation in a target nucleic acid sequence. As described above, the cleavage of the PTO hybridized with a matching template may be induced at a site immediately adjacent in a 3'-direction to the 5'-end of the 3'-targeting portion of the PTO, for example, under upstream primer extension-dependent cleavage induction. The 3'-end of the PTO fragment has the complementary nucleotide to the single nucleotide variation. The PTO fragment is hybridized with a hCTO having a capturing portion comprising a sequence corresponding to the nucleotide variation and then extended to form the extended duplex. The extended duplex is hybridized with the IO to provide the target signal. If the same PTO is hybridized with a mismatching template having the identical sequence to the matching template except for the single nucleotide variation, the cleavage of the PTO may occur at a site two nucleotides apart in a 3'-direction from the 5'-end of the 3'-targeting portion of the PTO. The 3'-end of the PTO fragment has the further cleaved nucleotide than the complementary nucleotide to the single nucleotide variation. Where the site of the hCTO hybridized with the additional-cleaved nucleotide is designed to have a non-complementary sequence to the additional-cleaved nucleotide, the 3'-end of the PTO fragment is not hybridized with the hCTO, resulting in no extension of the PTO fragment in a controlled condition.

According to an embodiment, a cleavage site of the PTO having a complementary sequence to the nucleotide variation at its 5'-end part of the 3'-targeting portion is different depending on hybridization with a matching template or with a mismatching template, such that the PTO fragment released from either hybridization event has different sequence, for example, in its 3'-end part or in its 3'-end.

According to an embodiment, the selection of the nucleotide sequence of hCTO in consideration of the difference in 3'-end parts of the PTO fragments allows to discriminate the matching template from the mismatching template.

According to an embodiment, the production of either the PTO fragments may be distinctly detected by an extension reaction on the hCTO.

According to an embodiment, the hCTO has a sequence selected such that the hCTO is not hybridized with the additional 3'-end portion of the second fragment to prevent the second fragment from extension when the second fragment is hybridized with the capturing portion of the hCTO.

As described above, the extension of the first fragment is detected by hybridization of the hCTO-extended duplex with the IO.

According to an embodiment, the 5'-end part of the 3'-targeting portion of the PTO comprises a non-base pairing moiety located within 1-10 nucleotides (or 1-5 nucleotides) apart from the nucleotide variation discrimination site.

The non-base pairing moiety prevents the 5'-end part of the 3'-targeting portion from formation of a double strand with the target nucleotide sequence when the PTO is hybridized with the target nucleic acid sequence having the nucleotide variation non-complementary to the variation discrimination site. The use of the non-base pairing moiety (e.g., artificial mismatch nucleotide) enhances discrimination potential of the PTO to nucleotide variations.

According to an embodiment, the non-base pairing moiety does not inhibit the formation of a double strand between the 5'-end part of the 3'-targeting portion of the PTO and the target nucleic acid sequence when the PTO is hybridized with the target nucleic acid sequence having the nucleotide variation complementary to the nucleotide variation discrimination site.

According to an embodiment, the non-base pairing moiety widens the distance between the initial cleavage site on the hybrid of the PTO and the matching template and the initial cleavage site on the hybrid of the PTO and the mismatching template.

According to an embodiment, the introduction of a non-base paring moiety sequence enables the initial cleavage site to be adjusted, particularly the initial cleavage site on the hybrid of the PTO and the mismatching template.

According to an embodiment, the non-base pairing moiety is located downstream of the nucleotide variation discrimination site.

The non-base pairing moiety includes any moieties not forming a base pair between target nucleic acid sequences. The non-base pairing moiety may be (i) a nucleotide comprising an artificial mismatch base, a natural/non-natural base incapable of base-pairing, a base modified to be incapable of base pairing or a universal base, (ii) a non-base pairing nucleotide modified to be incapable of base pairing, or (iii) a non-base pairing chemical compound.

For example, the non-base pairing moiety includes alkylene group, ribofuranosyl naphthalene, deoxy ribofuranosyl naphthalene, metaphosphate, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage and aryl phosphoroamidate linkage. Conventional carbon spacers are also used as non-base pairing moieties. Universal bases as non-base pairing moieties are useful in adjusting cleavage sites of the PTO.

As base pairs containing universal bases such as deoxyinosine, 1-(2'-deoxy-beta-D-ribofuranosyl)-3-nitropyrrole and 5-nitroindole have a lower binding strength than those between natural bases, universal bases may be employed as non-base pairing moieties under certain hybridization conditions.

The non-base pairing moiety introduced into the 5'-end part comprises 1-10, 1-5 or 1-2 moieties. A plurality of non-base pairing moieties in the 5'-end part may be present in a consecutive or intermittent manner. In certain embodiment, the non-base pairing moiety comprises 2-5 consecutive moieties.

In certain embodiment, the non-base pairing moiety is a non-base pairing chemical compound.

According to an embodiment, the nucleotide variation discrimination site and the non-base pairing moiety of the PTO are located within 10 nucleotides, 8 nucleotides, 7 nucleotides, 6 nucleotides, 5 nucleotides, 4 nucleotides, 3 nucleotides, 2 nucleotides or 1 nucleotide apart from the 5'-end of the 3'-targeting portion.

Where a probe comprising both at its 5'-end a non-complementary tail to a target nucleic acid sequence and at its 5'-end portion a nucleotide variation discrimination site is hybridized with a mismatch template to a nucleotide at the nucleotide variation discrimination site, the 5'-end portion may form a single strand and the other portions may form a double strand with the target nucleic acid sequence. While such a probe is different from the PTO in terms of probe design, it may be considered as probes having the PTO structure upon hybridization with mismatching templates. Therefore, signal may be generated by the present analysis method using the PTO. The application may be useful in detection of target nucleic acid sequences having a nucleotide variation non-complementary to the nucleotide variation discrimination site of probes.

The PCE-hCTO assay in conjunction with preferential amplification methods using an amplification blocker may effectively detect nucleotide variations in minority.

Clinical samples usually contain the wild-type allele in abundance and the mutant allele in minority. In an amplification step, the amplification of the abundant wild-type allele is likely to consume most reagents for amplification and therefore the mutant allele is not amplified to prohibit signal generation. For overcoming the shortcomings, there have been suggestions to selectively amplify the mutant allele with preventing amplification of the wild-type allele.

Representatively, methods using oligonucleotides containing PNA or LNA as an amplification blocker have been reported (US 2004/0014105, U.S. Pat. Nos. 7,803,543, 8,206,929, H. Orum., Nucleic Acids Research 21:5332-5336 (1993) A. Senescau et al., Journal of Clinical Microbiology, 3304-3308(2005), Y. Nagai et al., Cancer Res 65:7276-7282 (2005), Henrik et al., Nucleic Acid Research 21:5332-5336 (1993) and Luo et al., Nucleic Acid Research Vol. 34, No 2 e12 (2006)). These methods have been called as "clamping method".

In general, the amplification blockers for clamping are hybridized only with templates having perfectly complementary sequence to the amplification blockers under the same condition, which are designed not to be hybridized with templates having even single mismatch. The template hybridized with the amplification blocker inhibiting primer annealing or chain elongation is not amplified and only that not hybridized with the amplification blocker is amplified. Nucleic acid analogues such as PNA and LNA are useful as amplification blockers in the senses that they show significant $T_m$ differences for even a single base difference.

Where polymerases used have nuclease activity, the amplification blocker is required to possess resistant to nucleases activity.

Where two variant types which have different sequences from each other in a nucleotide variation region of a target nucleic acid sequence are present in a sample, the amplification blocker permits to amplify a target nucleic acid sequence having the nucleotide variation of interest and not to amplify a target nucleic acid sequence having the other nucleotide variation, enabling to detect the nucleotide variation of interest in more efficient manner. In particular, the utilization of amplification blocker is very useful in detection of the mutant allele in minority from clinical samples containing the wild-type allele in abundance and the mutant allele in minority.

Although the amplification blocker is used, the amplification of the wild-type allele may be not completely prevented. However, the PCE-hCTO assay using the PTO with excellent discrimination potential to nucleotide variations allows to detect mutant alleles in minority that are hardly detected by conventional technologies.

In certain embodiment, the amplification blocker located downstream of a primer blocks extension of the primer.

In certain embodiment, the amplification blocker is an oligonucleotide prepared with natural nucleoside/nucleotide, nucleoside/nucleotide analogue or their combination.

In certain embodiment, the amplification blocker comprises nucleosides/nucleotides having a backbone resistant to 5' nuclease activity. The nucleosides/nucleotides with a backbone resistant to the 5' nuclease activity include any one known to one of skill in the art. For example, it includes various phosphorothioate linkages, phosphonate linkages, phosphoroamidate linkages and 2'-carbohydrates modifications. In certain embodiment, nucleotides having a backbone resistant to the 5' nuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

According to an embodiment, the amplification blocker comprises peptide nucleic acid (PNA), locked nucleic acid (LNA), Morpholino, glycol nucleic acid (GNA), threose nucleic acid (TNA), bridged nucleic acids (BNA), N3'-P5' phosphoramidate (NP) oligomers, minor groove binder-linked-oligonucleotides (MGB-linked oligonucleotides), phosphorothioate (PS) oligomers, $C_1$-$C_4$ alkylphosphonate oligomers, phosphoramidates, β-phosphodiester oligonucleotides, a-phosphodiester oligonucleotides or combination thereof.

In certain embodiment, the amplification blocker has resistance to 5' nuclease activity and its $T_m$ value in hybridization is greatly affected by even by a single mismatch. Representative examples having the afore-mentioned properties are amplification blockers containing PNA or LNA.

The amplification blocker may have any length. For instance, the amplification blocker is 5-100 nucleotides, 5-80 nucleotides, 5-50 nucleotides, 5-40 nucleotides, 5-nucleotides, 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length.

In certain embodiment, the amplification blocker is blocked at its 3'-end to prohibit its extension.

The nucleotide variation discrimination site of the amplification blocker to be opposite to the nucleotide variation region on the target nucleic acid sequence may be located on any site of the amplification blocker, so long as it inhibits the amplification of the target nucleic acid sequence having the non-target nucleotide variation but does not inhibit the amplification of the target nucleic acid sequence having the target nucleotide variation.

According to an embodiment, the nucleotide variation discrimination site of the amplification blocker comprises a nucleotide sequence complementary to the non-target nucleotide variation.

In certain embodiment, the nucleotide variation discrimination site of the amplification blocker may be located at its 5'-end portion, middle portion or 3'-end portion.

The amplification blocker may be more than 200 nucleotides, more than 100 nucleotides, more than 50 nucleotides, more than 30 nucleotides, more than 20 nucleotides, more than 10 nucleotides, more than 5 nucleotides, more than 2 nucleotides, or more than 1 nucleotide apart from a primer that is located upstream of the amplification blocker. The amplification blocker may be immediately adjacent to the primer.

Where the PCE-hCTO assay in conjunction with the amplification blocker is employed to detect nucleotide variation, the PTO and the amplification blocker may be designed to be located on the same strand or different strands of the double strand of a target nucleic acid sequence. Where designed to be located on the same strand, the PTO and the amplification blocker may be interactively affected in hybridization with a target nucleic acid sequence and adjustment of reaction conditions or sequences may be required.

According to an embodiment, the target nucleic acid sequence used in the present invention is a pre-amplified nucleic acid sequence by an amplification primer.

The advantages of the present invention may be highlighted in the simultaneous (multiplex) detection of at least two target nucleic acid sequences.

According to an embodiment, the method is performed to detect at least two types of target nucleic acid sequences; wherein the upstream oligonucleotide comprises at least two types of oligonucleotides, the PTO comprises at least two types of the PTOs, the hCTO comprises at least two types of the hCTOs, and the IO comprises at least two types of the IOs.

According to an embodiment, the present invention is performed using at least two types of downstream primers to the PTO.

The target nucleic acid sequence to be detected by the present invention includes a wide variety of nucleic acid sequences, e.g., sequences in a genome, artificially isolated or fragmented sequences and synthesized sequences (e.g., cDNA sequences and barcode sequences). For instance, the target nucleic acid sequence includes nucleic acid marker sequences for Immuno-PCR (IPCR). IPCR employs conjugates between nucleic acid marker sequences and antibodies together with PCR, which is widely applied for detecting various types of targets including proteins (see Sano et al., Science 258 pp: 120-122(1992), U.S. Pat. No. 5,665,539, Niemeyer et al., Trends in Biotechnology 23 pp: 208-216 (2005), U.S. Pat. Pub. No. 2005/0239108 and Ye et al., Journal of Environmental Science 22 pp: 796-800(2010)). The target nucleic acid molecule of the present invention includes nucleic acid markers as used in IPCR method and the present invention may be applied to detect nucleic acid markers in IPCR method.

II. Embodiments with Amplification of Target Nucleic Acid Sequences

In another aspect of this invention, there is provided a method for detecting a target nucleic acid sequence from a DNA or a mixture of nucleic acids by a PCE-hCTO (PTO Cleavage and Extension using hCTO) assay on a solid phase, comprising:

(a) hybridizing the target nucleic acid sequence with a primer pair comprising an upstream primer and a downstream primer and a PTO (Probing and Tagging Oligonucleotide); wherein each of the upstream primer and the downstream primer comprise a hybridizing nucleotide sequence complementary to the target nucleic acid sequence; the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence; the PTO is located between the upstream primer and the downstream primer; wherein the PTO is blocked at its 3'-end to prohibit its extension;

(b) contacting the resultant of the step (a) to a template-dependent nucleic acid polymerase having a 5' nuclease activity under conditions for extension of the primers and for cleavage of the PTO; wherein when the PTO is hybridized with the target nucleic acid sequence, the upstream primer is extended and the extended strand induces cleavage of the PTO by the template-dependent nucleic acid polymerase having the 5' nuclease activity such that the cleavage releases a fragment comprising the 5'-tagging portion or a part of the 5'-tagging portion of the PTO;

(c) hybridizing the fragment released from the PTO with a hybridizing-capturing and templating oligonucleotide (hCTO); wherein the hCTO comprises (i) a CTO in a 3' to 5' direction comprising a capturing portion comprising a nucleotide sequence complementary to the 5'-tagging portion or a part of the 5'-tagging portion of the PTO and a templating portion comprising a nucleotide sequence non-complementary to the 5'-tagging portion and the 3'-targeting portion of the PTO, and (ii) at the 3'- or 5'-end of the CTO an IO-hybridizing portion comprising a nucleotide sequence complementary to an immobilized oligonucleotide (IO) immobilized on a solid substrate; wherein the fragment released from the PTO is hybridized with the capturing portion of the hCTO;

(d) performing an extension reaction using the resultant of the step (c) and a template-dependent nucleic acid polymerase; wherein the fragment hybridized with the capturing portion of the hCTO is extended to form an extended duplex; wherein the extended duplex has a $T_m$ value adjustable by (i) a sequence and/or length of the fragment, (ii) a sequence and/or length of the hCTO or (iii) the sequence and/or length of the fragment and the sequence and/or length of the hCTO; wherein the IO-hybridizing portion of the hCTO remains in a single strand state;

(e) hybridizing the IO with the IO-hybridizing portion of the hCTO in the single strand state; wherein the IO immobilized on the solid substrate comprises a nucleotide sequence complementary to the IO-hybridizing portion of the hCTO; wherein the IO is hybridized with the IO-hybridizing portion of the hCTO to form an IO duplex; wherein the extended duplex provides a target signal by (i) at least one label linked to the fragment and/or the hCTO, (ii) a label incorporated into the extended duplex during the extension reaction, (iii) a label incorporated into the extended duplex during the extension reaction and a label linked to the fragment and/or the hCTO, or (iv) a label linked to the fragment or incorporated into the extended duplex during the extension reaction and a label linked to the IO; and (f) detecting the extended duplex on the solid phase by measuring the target signal at a pre-determined temperature at which both the extended duplex and the IO duplex is in a double strand state; wherein the presence of the extended duplex indicates the presence of the target nucleic acid sequence.

Since the embodiment of the PCE-hCTO assay accompanied by amplification reaction follows the PCE-hCTO assay described above except for using a primer pair in the step (a), the common descriptions between them are omitted in order to avoid undue redundancy leading to the complexity of this specification.

According to an embodiment, the method further comprises repeating at least twice all or some (e.g., steps (a)-(b), (a)-(d) or (a)-(e)) of the steps (a)-(f) with denaturation between repeating cycles. The reaction repetition may be at least five, ten, twenty or thirty times, and no more than seventy, sixty, fifty or forty times.

III. PCE-hCTO Assay Based on Upstream Oligonucleotide-Independent 5' Nuclease Activity In still another aspect of this invention, there is provided a method for detecting a target nucleic acid sequence from a DNA or a mixture of nucleic acids by a PCE-hCTO (PTO Cleavage and Extension using hCTO) assay on a solid phase, comprising:

(a) hybridizing the target nucleic acid sequence with a PTO (Probing and Tagging Oligonucleotide); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion is hybridized with the target nucleic acid sequence and the 5'-tagging portion is not hybridized with the target nucleic acid sequence;

(b) contacting the resultant of the step (a) to an enzyme having a 5' nuclease activity under conditions for cleavage of the PTO; wherein the PTO is hybridized with the target nucleic acid sequence, the PTO is cleaved by the enzyme having the 5' nuclease activity such that the cleavage releases a fragment comprising the 5'-tagging portion or a part of the 5'-tagging portion of the PTO;

(c) hybridizing the fragment released from the PTO with a hybridizing-capturing and templating oligonucleotide (hCTO); wherein the hCTO comprises (i) a CTO in a 3' to 5' direction comprising a capturing portion comprising a nucleotide sequence complementary to the 5'-tagging portion or a part of the 5'-tagging portion of the PTO and a templating portion comprising a nucleotide sequence non-complementary to the 5'-tagging portion and the 3'-targeting portion of the PTO, and (ii) at the 3'- or 5'-end of the CTO an IO-hybridizing portion comprising a nucleotide sequence complementary to an immobilized oligonucleotide (IO) immobilized on a solid substrate; wherein the fragment released from the PTO is hybridized with the capturing portion of the hCTO;

(d) performing an extension reaction using the resultant of the step (c) and a template-dependent nucleic acid polymerase; wherein the fragment hybridized with the capturing portion of the hCTO is extended to form an extended duplex; wherein the extended duplex has a $T_m$ value adjustable by (i) a sequence and/or length of the fragment, (ii) a sequence and/or length of the hCTO or (iii) the sequence and/or length of the fragment and the sequence and/or length of the hCTO; wherein the IO-hybridizing portion of the hCTO remains in a single strand state;

(e) hybridizing the IO with the IO-hybridizing portion of the hCTO in the single strand state; wherein the IO immobilized on the solid substrate comprises a nucleotide sequence complementary to the IO-hybridizing portion of the hCTO; wherein the IO is hybridized with the IO-hybridizing portion of the hCTO to form an IO duplex; wherein the extended duplex provides a target signal by (i) at least one label linked to the fragment and/or the hCTO, (ii) a label incorporated into the extended duplex during the extension reaction, (iii) a label incorporated into the extended duplex during the extension reaction and a label linked to the fragment and/or the hCTO, or (iv) a label linked to the fragment or incorporated into the extended duplex during the extension reaction and a label linked to the IO; and (f) detecting the extended duplex on the solid phase by measuring the target signal at a pre-determined temperature at which both the extended duplex and the IO duplex is in a double strand state; wherein the presence of the extended duplex indicates the presence of the target nucleic acid sequence.

Since the present method based on upstream oligonucleotide-independent 5' nuclease activity is the same as those by the PCE-hCTO assay using upstream oligonucleotides except for no use of upstream oligonucleotides, the common descriptions between them are omitted in order to avoid undue redundancy leading to the complexity of this specification.

Interestingly, the present method based on upstream oligonucleotide-independent 5' nuclease activity practically provides target signals by the PCE-hCTO assay even no use of upstream oligonucleotides.

For the present method, conventional enzymes having upstream oligonucleotide-independent 5' nuclease activity may be used. Among template-dependent polymerases having 5' nuclease activity, there are several enzymes having upstream oligonucleotide-independent 5' nuclease activity, e.g., TaqDNA polymerase.

Considering amplification of target nucleic acid sequences and cleavage efficiency of the PTO, the PCE-hCTO assay of the present invention is preferably performed using upstream oligonucleotides.

According to an embodiment, the method further comprises repeating at least twice all or some (e.g., steps (a)-(b), (a)-(d) or (a)-(e)) of the steps (a)-(f) with denaturation between repeating cycles. The reaction repetition may be at least five, ten, twenty or thirty times, and no more than seventy, sixty, fifty or forty times.

IV. Kits for Target Detection

In a further aspect of this invention, there is provided a kit for detecting a target nucleic acid sequence from a DNA or a mixture of nucleic acids by a PCE-hCTO (PTO Cleavage and Extension using hCTO) assay on a solid phase, comprising:

(a) an upstream oligonucleotide comprising a hybridizing nucleotide sequence complementary to the target nucleic acid sequence;

(b) a probing and targeting oligonucleotide (PTO); wherein the PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the 3'-targeting portion of the PTO is hybridized with the target nucleic acid sequence and the 5'-tagging portion is not hybridized with the target nucleic acid sequence; the upstream oligonucleotide is located upstream of the PTO; wherein the upstream oligonucleotide or its extended strand induces cleavage of the PTO by an enzyme having a 5' nuclease activity such that the cleavage releases a fragment comprising the 5'-tagging portion or a part of the 5'-tagging portion of the PTO;

(c) a hybridizing-capturing and templating oligonucleotide (hCTO); wherein the hCTO comprises (i) a CTO in a 3' to 5' direction comprising a capturing portion comprising a nucleotide sequence complementary to the 5'-tagging portion or a part of the 5'-tagging portion of the PTO and a templating portion comprising a nucleotide sequence non-complementary to the 5'-tagging portion and the 3'-targeting portion of the PTO, and (ii) at the 3'- or 5'-end of the CTO an IO-hybridizing portion comprising a nucleotide sequence complementary to an immobilized oligonucleotide (IO) immobilized on a solid substrate; wherein the fragment released from the PTO is hybridized with the capturing portion of the hCTO; wherein the fragment hybridized with the capturing portion of the hCTO is extended by a template-dependent nucleic acid polymerase to form an extended duplex; and (d) an IO immobilized on the solid substrate comprising a nucleotide sequence complementary to the IO-hybridizing portion of the hCTO; wherein the IO is hybridized with the IO-hybridizing portion of the hCTO to form an IO duplex.

Since the kit of this invention is constructed to perform the detection method of the present invention described above, the common descriptions between them are omitted in order to avoid undue redundancy leading to the complexity of this specification.

In certain embodiment, when the IO-hybridizing portion is located at the 5'-end of the CTO, the hCTO further comprises a blocker portion between the CTO and the IO-hybridizing portion to prevent extension reaction of the fragment.

In an embodiment, the kit further comprises an enzyme having a 5' nuclease activity.

In an embodiment, the kit further comprises a template-dependent nucleic acid polymerase.

In an embodiment, the kit further comprises a template-dependent nucleic acid polymerase having a 5' nuclease activity.

In an embodiment, the fragment and/or the hCTO has at least one label. In an embodiment, the label is a single label or interactive dual label.

In an embodiment, the kit further comprises a label to be incorporated into the extended duplex during the extension reaction.

In an embodiment, the kit further comprises a label to be incorporated into the extended duplex during the extension reaction and the fragment and/or the hCTO has at least one label.

In an embodiment, the fragment has a label or the kit further comprises a label to be incorporated into the extended duplex during the extension reaction, and the IO has a label.

In an embodiment, the PTO, hCTO and/or IO is blocked at its 3'-end to prohibit its extension.

In an embodiment, the kit is used to detect at least two types of target nucleic acid sequences; wherein the upstream oligonucleotide comprises at least two types of oligonucleotides, the PTO comprises at least two types of the PTOs, the hCTO comprises at least two types of the hCTOs, and the IO comprises at least two types of the IOs.

In an embodiment, the IO is immobilized through its 5'-end or 3'-end onto a solid substrate.

In an embodiment, the kit further comprises a downstream primer.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

The features and advantages of this invention will be summarized as follows:

(a) The present invention firstly hybridizes the PTO with a target nucleic acid sequence, forms the extended duplex in a target-dependent manner by using the hCTO having artificially selected sequence as templates and finally hybridizes the extended strand with the IO immobilized on a solid phase. In other words, the present invention employs a series of reactions including PTO hybridization and cleavage, hCTO hybridization and extension and IO hybridization, which is responsible for the highly enhanced specificity of the present invention.

(b) Conventional approach performing an extension reaction on an oligonucleotide immobilized on a solid substrate is unlikely to effectively produce reaction results because a solid phase may provide restricted reaction environment.

According to the present invention, the extended duplex is formed in a liquid phase in a target-dependent manner and then its presence is detected on a solid phase. Since hCTO is not immobilized onto a solid phase, the extended duplex is more effectively formed in a liquid phase.

(c) The presence or absence of the extended duplex is detected on a solid phase by using hybridization between the extended duplex and the IO immobilized onto a solid phase. Therefore, the present invention can simultaneously detect a plurality of target nucleic acid sequences even using a single type of signaling systems.

(d) Where the IO comprising a complementary sequence to one strand of the extended duplex is used, the hybridization between the IO and the extended duplex is likely to be prevented by the presence of the other stand of the extended duplex. The present invention completely overcomes such problems by using hCTO enabling to have a single strand portion in the extended duplex, thereby ensuring more effective hybridization between the IO and the extended duplex.

(e) In the present invention, the hybridization of the IO with the extended duplex or only hCTO is determined by measuring the generation, extinguishment or change (decrease or increase) of a signal provided on a solid phase. The signal may be provided by a label linked to the fragment, the hCTO or IO and/or extension-dependent incorporating label.

(f) The present invention provides the target-dependent extended duplex having a predetermined $T_m$ value which is adjustable by (i) a sequence and/or length of the fragment, (ii) a sequence and/or length of the hCTO or (iii) the sequence and/or length of the fragment and the sequence and/or length of the hCTO. Also, the $T_m$ value of the IO duplex formed by hybridization between the IO and the IO-hybridizing portion of the hCTO can be variously adjusted.

(g) It is noteworthy that the sequence of the 5'-tagging portion of PTO, the sequence of hCTO and the sequence of the IO can be selected with no consideration of target nucleic acid sequences. This makes it possible to pre-design a pool of sequences for the 5'-tagging portion of PTO, the hCTO and the IO. Although the 3'-targeting portion of the PTO has to be prepared with considering target nucleic acid sequences, the hCTO and IO can be prepared in a ready-made fashion with no consideration or knowledge of target nucleic acid sequences.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Evaluation of PCE-hCTO Assay Using hCTO Having IO-Hybridizing Portion at its 5'-End Portion We examined whether PCE-hCTO assay using the single-labeled PTO (Probing and Tagging Oligonucleotide), hCTO (Hybridizing Capturing and Templating Oligonucleotide), and the immobilized oligonucleotide (IO) on microarray can detect a target nucleic acid sequence.

Taq DNA polymerase having a 5' nuclease activity was used for the extension of upstream primer and downstream primer, the cleavage of PTO, and the extension of PTO fragment. Genomic DNA of *Neisseria gonorrhoeae* (NG) was used as a target nucleic acid sequence.

The PTO having a fluorescent molecule (Quasar570) at its 5'-end is blocked with a carbon spacer at its 3'-end. The hCTO having IO-hybridizing portion at its 5'-end portion has a blocker both at its 3'-end and in between IO-hybridization portion and templating portion. IO has poly(T)$_{10}$ as a linker arm and was immobilized on the surface of a glass slide by using an amino group (AminnoC7) at its 3'-end. A marker probe having a fluorescent reporter molecule (Quasar570) at its 5'-end was immobilized on the surface of the glass slide by using an amino group (AminnoC7) at its 3'-end.

In this Example, if NG is present, a PTO specifically hybridized to NG is cleaved and a fluorescent reporter-labeled PTO fragment is produced. The PTO fragment is annealed to the capturing portion of the hCTO, extended on the templating portion of the hCTO before the position opposite of the blocker located between IO-hybridization portion and templating portion, and forms the fluorescent reporter-labeled hCTO-extended duplex having a single-stranded IO-hybridizing portion. The hCTO-extended duplex hybridizes IO on microarray by using its single-stranded IO-hybridization portion, generating fluorescent signal on the spot. However, if NG is not present, hCTO does not form the fluorescent reporter-labeled hCTO-extended duplex, and the hCTO does not generating fluorescent signal on the spot even if the hCTO hybridizes IO on microarray.

Therefore, the evaluation of the presence or the absence of the fluorescent signal on the spot can determine the existence of the target nucleic acid sequence. The cleavage of PTO and the extension of PTO fragment, the hybridization of the hCTO-extended duplex to IO were conducted simultaneously on the microarray. After the reaction, the presence or absence of the fluorescent reporter-labeled hCTO duplex with IO was analyzed.

The sequences of upstream primer, downstream primer, PTO, hCTO, IO, and marker used in this Example are:

```
NG-F
                                         (SEQ ID NO: 1)
5'-TACGCCTGCTACTTTCACGCTIIIIIGTAATCAGATG-3'

NG-R
                                         (SEQ ID NO: 2)
5'-CAATGGATCGGTATCACTCGCIIIIICGAGCAAGAAC-3'

PTO
                                         (SEQ ID NO: 3)
5'-[Quasar570]ACGACGGCTTGGCTGCCCCTCATTGGCGT
GTTTCG[C3 spacer]-3'
```

-continued

```
hCTO-1
                                        (SEQ ID NO: 4)
5'-TCCTGCTCGTCCTCGTGCTCTTAGGT[Spacer 18]AGG
GTATCCAGCGCTCAGCCAAGCCGTCGT[C3 spacer]-3'

IO-1
                                        (SEQ ID NO: 5)
5'-ACCTAAGAGCACGAGGACGAGCAGGATTTTTTTTTT
[AminoC7]-3'

Marker
                                        (SEQ ID NO: 6)
5'-[Quasar570]ATATATATAT[Amino C7]-3'
(I: Deoxyinosine)
(Underlined letters indicate the 5'-tagging
portion of PTO)
```

NSB9 NHS slides (NSBPOSTECH, Korea) were used for fabrication of the IO and marker (SEQ ID NOs: 5 and 6). The IO and marker dissolved in NSB spotting buffer at the final concentration of 50 μM were printed on the NSB9 NHS slides with PersonalArrayer™16 Microarray Spotter (CapitalBio, China). The IO and marker were spotted side by side in a 3×1 format (triplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound IO and marker and rinsed with distilled water. Then, the DNA-functionalized slides were dried using a slide centrifuge and stored in dark at 4° C. until use.

The PCE-hCTO reaction was conducted in the final volume of 30 μl containing 100 pg of genomic DNA of NG, 10 pmole of upstream primer (SEQ ID NO: 1), 10 pmole of downstream primer (SEQ ID NO: 2), 5 pmole of PTO (SEQ ID NO: 3), 0.5 pmole of hCTO (SEQ ID NO: 4) and 15 μl of 2× Master Mix [containing 2.5 mM MgCl$_2$, 200 μM of dNTPs, and 2.4 units of H-Taq DNA polymerase (Solgent, Korea)]; the whole mixture was applied to a chamber assembled on the surface of NSB glass slide on which the IO (SEQ ID NO: 5) was cross-linked. The slide was placed on in situ block in a thermocycler (GenePro B4I, China). The PCE-hCTO reaction was carried out as follows: 15 min denaturation at 95° C., 40 cycles of 30 sec at 95° C. and 60 sec at 55° C., and 30 min hybridization at 55° C.

After the reaction, the slides were washed in distilled water for 1 min at 60° C. We selected temperature at which the hybrid between the uncleaved PTO and the hCTO was removed by washing. The image acquisition was carried out by the use of Confocal Laser Scanner, Axon GenePix4300A (Molecular Device, US) with scanning at 5-μm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was triplicated for the test of reproducibility. The fluorescence intensity indicates the average value of the triplicated spots.

As shown in FIGS. 4A-4B, the fluorescent intensity was apparently increased in the presence of the target in comparison to that in the absence of the target. This result shows that PCE-hCTO assay using the single-labeled PTO, hCTO, and IO on microarray can detect a target nucleic acid sequence.

Example 2: Evaluation of PCE-hCTO Assay Using hCTO Having IO-Hybridizing Portion at its 3'-End Portion We examined whether PCE-hCTO assay using the single-labeled PTO, hCTO having IO-hybridizing portion at its 3'-end, and the IO on microarray can detect a target nucleic acid sequence.

TaqDNA polymerase having a 5' nuclease activity was used for the extension of upstream primer and downstream primer, the cleavage of PTO, and the extension of PTO fragment. Genomic DNA of *Neisseria gonorrhoeae* (NG) was used as a target nucleic acid sequence.

The PTO having a fluorescent molecule (Quasar570) at its 5'-end is blocked with a carbon spacer at its 3'-end. The hCTO and IO has a blocker at its 3'-end. IO has poly(T)$_{10}$ as a linker arm and was immobilized on the surface of a glass slide by using an amino group (AminnoC6) at its 5'-end. A marker probe having a fluorescent reporter molecule (Quasar570) at its 5'-end was immobilized on the surface of the glass slide by using an amino group (AminnoC7) at its 3'-end.

In this Example, if NG is present, a PTO specifically hybridized to NG is cleaved and a fluorescent reporter-labeled PTO fragment is produced. The PTO fragment is annealed to the capturing portion of the hCTO, extended on the templating portion of the hCTO, and forms the fluorescent reporter-labeled hCTO duplex having a single-stranded IO-hybridizing portion. The hCTO duplex hybridizes on microarray by using its single-stranded IO-hybridization portion, generating fluorescent signal on the spot. However, if NG is not present, hCTO does not form the fluorescent reporter-labeled hCTO duplex, and the hCTO does not generating fluorescent signal on the spot even if the hCTO hybridizes IO on microarray.

Therefore, the evaluation of the presence or the absence of the fluorescent signal on the spot can determine the existence of the target nucleic acid sequence. The cleavage of PTO and the extension of PTO fragment, the hybridization of the hCTO duplex to IO were conducted simultaneously on the microarray. After the reaction, the presence or absence of the fluorescent reporter-labeled hCTO duplex with IO was analyzed.

The sequences of upstream primer, downstream primer, PTO, hCTO, IO, and marker used in this Example are:

```
NG-F
                                        (SEQ ID NO: 1)
5'-TACGCCTGCTACTTTCACGCTIIIIIGTAATCAGATG-3'

NG-R
                                        (SEQ ID NO: 2)
5'-CAATGGATCGGTATCACTCGCIIIIICGAGCAAGAAC-3'

PTO
                                        (SEQ ID NO: 3)
5'-[Quasar570]ACGACGGCTTGGCTGCCCCTCATTGGCGT
GTTTCG[C3 spacer]-3' hCTO-2
                                        (SEQ ID NO: 7)
5'-AGGGTATCCAGCGCTCAGCCAAGCCGTCGTTTTTCCTGCT
CGTCCTCGTGCTCTTAGGT[C3 spacer]-3'

IO-2
                                        (SEQ ID NO: 8)
5'-[AminoC6]TTTTTTTTTTACCTAAGAGCACGAGGACGAG
CAGGA[C3 spacer]-3'
```

```
Marker
                                              (SEQ ID NO: 6)
5'-[Quasar570]ATATATATAT[Amino C7]-3'
(I: Deoxyinosine)
(Underlined letters indicate the 5'-tagging
portion of PTO)
```

NSB9 NHS slides (NSBPOSTECH, Korea) were used for fabrication of the IO and marker (SEQ ID NOs: 6 and 8). The IO and marker dissolved in NSB spotting buffer at the final concentration of 50 μM were printed on the NSB9 NHS slides with PersonalArrayer™16 Microarray Spotter (CapitalBio, China). The IO and marker were spotted side by side in a 3×1 format (triplicate spots), and the resulting microarray was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound IO and marker and rinsed with distilled water. Then, the DNA-functionalized slides were dried using a slide centrifuge and stored in dark at 4° C. until use.

The PCE-hCTO reaction was conducted in the final volume of 30 μl containing 100 pg of genomic DNA of NG, 10 pmole of upstream primer (SEQ ID NO: 1), 10 pmole of downstream primer (SEQ ID NO: 2), 5 pmole of PTO (SEQ ID NO: 3), 0.5 pmole of hCTO (SEQ ID NO: 7) and 15 μl of 2× Master Mix [containing 2.5 mM MgCl$_2$, 200 μM of dNTPs, and 2.4 units of H-Taq DNA polymerase (Solgent, Korea)]; the whole mixture was applied to a chamber assembled on the surface of NSB glass slide on which the IO (SEQ ID NO: 8) was cross-linked. The slide was placed on in situ block in a thermocycler (GenePro B4I, China). The PCE-hCTO reaction was carried out as follows: 15 min denaturation at 95° C., 40 cycles of 30 sec at 95° C. and 60 sec at 55° C., and 30 min hybridization at 55° C.

After the reaction, the slides were washed in distilled water for 1 min at 60° C. We selected temperature at which the hybrid between the uncleaved PTO and the hCTO was removed by washing. The image acquisition was carried out by the use of Confocal Laser Scanner, Axon GenePix4300A (Molecular Device, US) with scanning at 5-μm pixel resolution. The fluorescence intensity was analyzed by the use of quantitative microarray analysis software, GenePix pro7.0 software (Molecular Device, US). The fluorescence intensity was expressed as spot-medians after local background subtractions. Each spot was triplicated for the test of reproducibility. The fluorescence intensity indicates the average value of the triplicated spots.

The fluorescent intensity was apparently increased in the presence of the target in comparison to that in the absence of the target. This result shows that PCE-hCTO assay using the single-labeled PTO, hCTO, and IO on microarray can detect a target nucleic acid sequence.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence from a DNA or a mixture of nucleic acids by a PCE-hCTO (PTO Cleavage and Extension using hCTO) assay on a solid phase, comprising:

(a) hybridizing the target nucleic acid sequence with an upstream oligonucleotide and a probing and targeting oligonucleotide (PTO); said upstream oligonucleotide comprising a hybridizing nucleotide sequence complementary to the target nucleic acid sequence; said PTO comprising (i) a 3'-targeting portion comprising a hybridizing nucleotide sequence complementary to the target nucleic acid sequence and (ii) a 5'-tagging portion comprising a nucleotide sequence non-complementary to the target nucleic acid sequence; wherein the PTO is 15-80 nucleotides in length, the 3'-targeting portion of the PTO is 10-50 nucleotides in length and the 5'-tagging portion of the PTO is 5-30 nucleotides in length; wherein the 3'-targeting portion of the PTO is hybridized with the target nucleic acid sequence and the 5'-tagging portion is not hybridized with the target nucleic acid sequence; and the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; wherein when the enzyme having a 5' nuclease activity is a FEN (flap endonuclease) nuclease, the FEN nuclease is a 5' flap-specific nuclease;

(c) hybridizing the fragment released from the PTO with a hybridizing-capturing and templating oligonucleotide (hCTO); said hCTO comprising (i) a CTO in a 3' to 5' direction comprising a capturing portion comprising a nucleotide sequence complementary to the 5'-tagging portion or a part of the 5'-tagging portion of the PTO and a templating portion comprising a nucleotide sequence non-complementary to the 5'-tagging portion and the 3'-targeting portion of the PTO, and (ii) at the 3'- or 5'-end of the CTO an JO-hybridizing portion comprising a nucleotide sequence complementary to an immobilized oligonucleotide (IO) immobilized on a solid substrate; wherein when the JO-hybridizing portion is located at the 5'-end of the CTO, said hCTO further comprising a blocker portion between the CTO and the JO-hybridizing portion to prevent extension reaction of the fragment such that the fragment is extended before a position opposite of the blocker portion; wherein the fragment released from the PTO is hybridized with the capturing portion of the hCTO;

(d) performing an extension reaction using the resultant of the step (c) and a template-dependent nucleic acid polymerase; wherein the fragment hybridized with the capturing portion of the hCTO is extended to form an extended duplex; wherein the extended duplex has a $T_m$ value adjustable by (i) a sequence and/or length of the fragment, (ii) a sequence and/or length of the hCTO or (iii) the sequence and/or length of the fragment and the sequence and/or length of the hCTO; wherein the JO-hybridizing portion of the hCTO remains in a single strand state;

(e) hybridizing the IO with the JO-hybridizing portion of the hCTO in the single strand state; said IO immobilized on the solid substrate comprising a nucleotide sequence complementary to the JO-hybridizing portion of the hCTO; wherein the IO is hybridized with the JO-hybridizing portion of the hCTO to form an IO duplex; wherein the extended duplex provides a target signal by (i) at least one label linked to the fragment and/or the hCTO, (ii) a label incorporated into the extended duplex during the extension reaction, (iii) a label incorporated into the extended duplex during the extension reaction and a label linked to the fragment and/or the hCTO, or (iv) a label linked to the fragment or incorporated into the extended duplex during the extension reaction and a label linked to the IO; and (f) detecting the extended duplex on the solid phase by measuring the target signal at a pre-determined temperature at which both the extended duplex and the IO duplex are in a double strand state; wherein the presence of the extended duplex indicates the presence of the target nucleic acid sequence; wherein the hybridization of the step (a) is performed under stringent conditions such that the 3'-targeting portion is hybridized with the target nucleic acid sequence and the 5'-tagging portion is not hybridized with the target nucleic acid sequence; the hybridization of the step (c) is performed under stringent conditions such that the fragment released from the PTO is hybridized with the capturing portion of the hCTO to provide a form suitable in extension of the fragment; and the hybridization of the step (e) is performed under stringent conditions such that the IO is hybridized with the JO-hybridizing portion of the hCTO in the single strand state to form the IO duplex.

2. The method according to claim 1, wherein the target signal is provided by the at least one label linked to the fragment and/or the hCTO.

3. The method according to claim 2, wherein the hCTO has an interactive dual label comprising a reporter molecule and a quencher molecule; wherein the extension of the fragment in the step (d) induces change of a signal from the interactive dual label to give the target signal.

4. The method according to claim 2, wherein the hCTO has an interactive dual label comprising a reporter molecule and a quencher molecule; wherein the hybridization of the fragment with the hCTO in the step (c) induces change of a signal from the interactive dual label to give the target signal and the extended duplex maintains the target signal.

5. The method according to claim 2, wherein the fragment has an interactive dual label comprising a reporter molecule and a quencher molecule; wherein the hybridization of the fragment with the hCTO in the step (c) induces change of a signal from the interactive dual label to give the target signal and the extended duplex maintains the target signal.

6. The method according to claim 2, wherein the fragment has one of an interactive dual label comprising a reporter molecule and a quencher molecule and the hCTO has the other of the interactive dual label; wherein the hybridization of the fragment with the hCTO in the step (c) induces change of a signal from the interactive dual label to give the target signal and the extended duplex maintains the target signal.

7. The method according to claim 2, wherein the hCTO has a single label and the extension of the fragment in the step (d) induces change of a signal from the single label to give the target signal.

8. The method according to claim 2, wherein the hCTO has a single label; wherein the hybridization of the fragment with the hCTO in the step (c) induces change of a signal from the single label to give the target signal and the extended duplex maintains the target signal.

9. The method according to claim 2, wherein the fragment has a single label.

10. The method according to claim 1, wherein the target signal is provided by a single label incorporated into the extended duplex during the extension reaction; wherein the incorporated single label is linked to a nucleotide incorporated during the extension reaction.

11. The method according to claim 1, wherein the target signal is provided by the label incorporated into the extended duplex during the extension reaction and the label linked to the fragment and/or the hCTO; wherein the label incorporated is linked to a nucleotide incorporated during the extension reaction; wherein the two labels are an interactive dual label of a reporter molecule and a quencher molecule; wherein the extension of the fragment in the step (d) induces change of a signal from the interactive dual label to give the target signal.

12. The method according to claim 1, wherein the target signal is provided by the label linked to the fragment or incorporated into the extended duplex during the extension reaction and the label linked to the IO; the label linked to the fragment or incorporated into the extended duplex during the extension reaction has one of an interactive dual label comprising a reporter molecule and a quencher molecule and the IO has the other of the interactive dual label; wherein the hybridization of the IO with the extended duplex in the step (e) induces change of a signal from the interactive dual label to give the target signal.

13. The method according to claim 1, said method further comprising repeating some or all of the steps (a)-(f) with denaturation between repeating cycles.

14. The method according to claim 1, wherein the steps (a)-(f) are performed in a reaction vessel or in separate reaction vessels.

15. The method according to claim 1, wherein the method is performed in the presence of a downstream primer.

\* \* \* \* \*

UNITED STATES PATENT AND TRADEMARK OFFICE
CERTIFICATE OF CORRECTION

Page 1 of 1

PATENT NO. : 11,447,814 B2
APPLICATION NO. : 15/028817
DATED : September 20, 2022
INVENTOR(S) : Jong Yoon Chun et al.

It is certified that error appears in the above-identified patent and that said Letters Patent is hereby corrected as shown below:

In the Claims

• Column 49, Line 22: change "3'- or 5'-end of the CTO an JO-hybridizing portion" to read "3'- or 5'-end of the CTO an IO-hybridizing portion"
• Column 49, Line 25: change "solid substrate; wherein when the JO-hybridizing por-" to read "solid substrate; wherein when the IO-hybridizing por-"
• Column 49, Line 28: change "and the JO-hybridizing portion to prevent extension" to read "and the IO-hybridizing portion to prevent extension"
• Column 49, Line 44: change "hybridizing the IO with the JO-hybridizing portion of" to read "hybridizing the IO with the IO-hybridizing portion of"
• Column 49, Line 47: change "sequence complementary to the JO-hybridizing portion" to read "sequence complementary to the IO-hybridizing portion"
• Column 49, Line 49: change "JO-hybridizing portion of the hCTO to form an IO" to read "IO-hybridizing portion of the hCTO to form an IO"

Signed and Sealed this
Third Day of January, 2023

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 37
<212> TYPE: DNA
<213> ORGANISM: Artificial Sequence
<220> FEATURE:
<223> OTHER INFORMATION: Artifically synthesized
<220> FEATURE:
<221> NAME/KEY: misc_feature
<222> LOCATION: (22)..(26)
<223> OTHER INFORMATION: n denotes deoxyinosine

<400> SEQUENCE: 1
tacgcctgct actttcacgc tnnnnngtaa tcagatg                              37

<210> SEQ ID NO 2
<211> LENGTH: 37
<212> TYPE: DNA
<213> ORGANISM: Artificial Sequence
<220> FEATURE:
<223> OTHER INFORMATION: Artifically synthesized
<220> FEATURE:
<221> NAME/KEY: misc_feature
<222> LOCATION: (22)..(26)
<223> OTHER INFORMATION: n denotes deoxyinosine

<400> SEQUENCE: 2
caatggatcg gtatcactcg cnnnnncgag caagaac                              37

<210> SEQ ID NO 3
<211> LENGTH: 35
<212> TYPE: DNA
<213> ORGANISM: Artificial Sequence
<220> FEATURE:
```

```
<223> OTHER INFORMATION: Artificially synthesized

<400> SEQUENCE: 3
acgacggctt ggctgcccct cattggcgtg tttcg                              35

<210> SEQ ID NO 4
<211> LENGTH: 56
<212> TYPE: DNA
<213> ORGANISM: Artificial Sequence
<220> FEATURE:
<223> OTHER INFORMATION: Artificially synthesized

<400> SEQUENCE: 4
tcctgctcgt cctcgtgctc ttaggtaggg tatccagcgc tcagccaagc cgtcgt       56

<210> SEQ ID NO 5
<211> LENGTH: 36
<212> TYPE: DNA
<213> ORGANISM: Artificial Sequence
<220> FEATURE:
<223> OTHER INFORMATION: Artificially synthesized

<400> SEQUENCE: 5
acctaagagc acgaggacga gcaggatttt tttttt                             36

<210> SEQ ID NO 6
<211> LENGTH: 10
<212> TYPE: DNA
<213> ORGANISM: Artificial Sequence
<220> FEATURE:
<223> OTHER INFORMATION: Artificially synthesized

<400> SEQUENCE: 6
atatatatat                                                          10

<210> SEQ ID NO 7
<211> LENGTH: 59
<212> TYPE: DNA
<213> ORGANISM: Artificial Sequence
<220> FEATURE:
<223> OTHER INFORMATION: Artificially synthesized

<400> SEQUENCE: 7
agggtatcca gcgctcagcc aagccgtcgt ttttcctgct cgtcctcgtg ctcttaggt    59

<210> SEQ ID NO 8
<211> LENGTH: 36
<212> TYPE: DNA
<213> ORGANISM: Artificial Sequence
<220> FEATURE:
<223> OTHER INFORMATION: Artificially synthesized

<400> SEQUENCE: 8
tttttttttt acctaagagc acgaggacga gcagga                             36
```